US00RE44704E

(19) United States
(12) Reissued Patent
Chari et al.

(10) Patent Number: US RE44,704 E
(45) Date of Reissued Patent: *Jan. 14, 2014

(54) COMPOSITIONS AND METHODS FOR TREATING CANCER USING IMMUNOCONJUGATES AND CHEMOTHERAPEUTIC AGENTS

(75) Inventors: Ravi V. J. Chari, Newton, MA (US); Walter A. Blättler, Brookline, MA (US)

(73) Assignee: Immunogen Inc., Waltham, MA (US)

( * ) Notice: This patent is subject to a terminal disclaimer.

(21) Appl. No.: 13/613,743

(22) Filed: Sep. 13, 2012

Related U.S. Patent Documents

Reissue of:
(64) Patent No.: 7,303,749
Issued: Dec. 4, 2007
Appl. No.: 09/671,995
Filed: Sep. 29, 2000

U.S. Applications:
(63) Continuation of application No. 13/349,078, filed on Jan. 12, 2012, now Pat. No. Re. 43,899, which is a continuation of application No. 12/631,508, filed on Dec. 4, 2009, now abandoned.

(60) Provisional application No. 60/157,051, filed on Oct. 1, 1999.

(51) Int. Cl.

| | |
|---|---|
| ***A61K 39/395*** | (2006.01) |
| ***A61K 31/21*** | (2006.01) |
| ***A61K 31/33*** | (2006.01) |
| ***A61K 31/40*** | (2006.01) |
| ***A61K 31/44*** | (2006.01) |
| ***A61K 31/337*** | (2006.01) |
| ***A61K 31/075*** | (2006.01) |
| ***A61K 31/09*** | (2006.01) |
| ***A61K 31/165*** | (2006.01) |
| ***A61K 31/166*** | (2006.01) |
| ***A61K 31/167*** | (2006.01) |
| ***A61K 31/122*** | (2006.01) |

(52) U.S. Cl.
USPC ..... 424/178.1; 424/179.1; 424/181.1; 424/182.1; 424/649; 514/185; 514/188; 514/279; 514/506; 514/510; 514/563; 514/579; 514/647; 514/656; 514/675; 514/676; 514/678; 514/680; 514/715; 514/722; 514/747; 514/753; 514/755; 514/758

(58) Field of Classification Search
None
See application file for complete search history.

(56) References Cited

U.S. PATENT DOCUMENTS

| | | | |
|---|---|---|---|
| 3,896,111 | A | 7/1975 | Kupchan et al. |
| 4,137,230 | A | 1/1979 | Hashimoto et al. |
| 4,151,042 | A | 4/1979 | Higashide et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,968,603 | A | 11/1990 | Slamon et al. |
| 4,981,979 | A | 1/1991 | Sivam |
| 5,183,884 | A | 2/1993 | Kraus et al. |
| 5,208,020 | A | 5/1993 | Chari et al. |
| 5,217,713 | A | 6/1993 | Iwasa et al. |
| 5,395,924 | A | 3/1995 | Blättler et al. |
| 5,416,064 | A | 5/1995 | Chari et al. |
| 5,480,968 | A | 1/1996 | Kraus et al. |
| 5,514,554 | A | 5/1996 | Bacus |
| 5,639,641 | A | 6/1997 | Pedersen et al. |
| 5,677,171 | A | 10/1997 | Hudziak et al. |
| 5,679,648 | A | 10/1997 | McCaffrey et al. |
| 5,705,157 | A | 1/1998 | Greene |
| 5,725,856 | A | 3/1998 | Hudziak |
| 5,747,261 | A | 5/1998 | King et al. |

(Continued)

FOREIGN PATENT DOCUMENTS

| | | |
|---|---|---|
| AU | 2003/259913 | 8/2003 |
| AU | 2003/247762 | 1/2004 |

(Continued)

OTHER PUBLICATIONS

Boni et al (Cancer, 1989, vol. 63, pp. 638-642).*

(Continued)

*Primary Examiner* — Karen Canella
(74) *Attorney, Agent, or Firm* — Sughrue Mion, PLLC

(57) ABSTRACT

The present invention is based on the discovery that the administration of at least one immunoconjugate and at least one chemotherapeutic agent provides an unexpectedly superior treatment for cancer. The present invention is directed to compositions comprising at least one immunoconjugate and at least one chemotherapeutic agent and to methods of treating cancer using at least one immunoconjugate and at least one chemotherapeutic agent. The present invention also provides methods of modulating the growth of selected cell populations, such as cancer cells, by administering a therapeutically effective amount of at least one chemotherapeutic agent and at least one immunoconjugate.

5 Claims, 11 Drawing Sheets

(56) References Cited

U.S. PATENT DOCUMENTS

| | | | | |
|---|---|---|---|---|
| 5,772,997 | A | 6/1998 | Hudziak et al. | |
| 5,783,186 | A | 7/1998 | Arakawa et al. | |
| 5,786,344 | A * | 7/1998 | Ratain et al. | 514/100 |
| 5,821,337 | A | 10/1998 | Carter | |
| 5,824,311 | A | 10/1998 | Greene et al. | |
| 5,837,234 | A | 11/1998 | Gentile et al. | |
| 5,840,525 | A | 11/1998 | Vandlen et al. | |
| 5,877,305 | A | 3/1999 | Huston et al. | |
| 5,919,815 | A | 7/1999 | Bradley et al. | |
| 5,968,517 | A | 10/1999 | Duncan et al. | |
| 6,022,541 | A | 2/2000 | Senger et al. | |
| 6,054,297 | A | 4/2000 | Carter et al. | |
| 6,333,410 | B1 | 12/2001 | Chari et al. | |
| 6,436,931 | B1 | 8/2002 | Chari et al. | |
| 6,441,163 | B1 | 8/2002 | Chari et al. | |
| 6,531,131 | B1 | 3/2003 | Gu et al. | |
| 6,632,979 | B2 | 10/2003 | Erickson et al. | |
| 6,949,245 | B1 | 9/2005 | Sliwkowski | |
| 7,030,231 | B1 | 4/2006 | Craik et al. | |
| 7,097,840 | B2 | 8/2006 | Erickson et al. | |
| 7,276,497 | B2 | 10/2007 | Chari et al. | |
| 7,303,749 | B1 | 12/2007 | Chari et al. | |
| 7,375,078 | B2 | 5/2008 | Feng | |
| 7,485,302 | B2 | 2/2009 | Adams et al. | |
| 7,498,030 | B2 | 3/2009 | Adams et al. | |
| 7,501,122 | B2 | 3/2009 | Adams et al. | |
| 7,537,931 | B2 | 5/2009 | Adams et al. | |
| 7,575,748 | B1 | 8/2009 | Erickson et al. | |
| 7,618,631 | B2 | 11/2009 | Sliwkowski | |
| 7,862,817 | B2 | 1/2011 | Adams et al. | |
| 2002/0001587 | A1 | 1/2002 | Erickson et al. | |
| 2003/0086924 | A1 | 5/2003 | Sliwkowski | |
| 2004/0013667 | A1 | 1/2004 | Kelsey et al. | |
| 2004/0235068 | A1 | 11/2004 | Levinson | |
| 2004/0241174 | A1 | 12/2004 | Amphlett et al. | |
| 2005/0133285 | A1 | 6/2005 | Shimizu | |
| 2005/0169933 | A1 | 8/2005 | Steeves et al. | |
| 2005/0238650 | A1 | 10/2005 | Crowley et al. | |
| 2005/0276812 | A1 | 12/2005 | Ebens et al. | |
| 2006/0216285 | A1 | 9/2006 | Adams et al. | |
| 2007/0092940 | A1 | 4/2007 | Eigenbrot et al. | |
| 2007/0184055 | A1 | 8/2007 | Sliwkowski | |
| 2007/0269429 | A1 | 11/2007 | Kelsey et al. | |
| 2007/0269446 | A1 | 11/2007 | de Sauvage et al. | |
| 2008/0085283 | A1 | 4/2008 | Levinson | |
| 2008/0114153 | A1 | 5/2008 | Steeves et al. | |
| 2008/0145374 | A1 | 6/2008 | Steeves et al. | |
| 2008/0166294 | A1 | 7/2008 | de Sauvage et al. | |
| 2008/0171040 | A1 | 7/2008 | Ebens et al. | |
| 2008/0171856 | A1 | 7/2008 | Steeves et al. | |
| 2008/0171865 | A1 | 7/2008 | Steeves et al. | |
| 2008/0226659 | A1 | 9/2008 | Erickson et al. | |
| 2009/0041791 | A1 | 2/2009 | Feng | |
| 2009/0202536 | A1 | 8/2009 | Ebens et al. | |
| 2011/0129464 | A1 | 6/2011 | Adams et al. | |

FOREIGN PATENT DOCUMENTS

| | | | |
|---|---|---|---|
| EP | 2004/25235 | | 5/1991 |
| EP | 0 563 475 | | 10/1993 |
| JP | 58-167592 | | 10/1983 |
| JP | 58-167592 | A | 10/1983 |
| JP | 62-195387 | | 8/1987 |
| JP | 62-195387 | A | 8/1987 |
| JP | 3161490 | | 7/1991 |
| JP | 10130168 | | 5/1998 |
| JP | 2001505951 | | 5/2001 |
| JP | 2002-541088 | | 12/2002 |
| JP | 2002-541088 | A | 12/2002 |
| JP | 2002-543093 | | 12/2002 |
| JP | 2002-543093 | A | 12/2002 |
| JP | 2003-503365 | | 1/2003 |
| JP | 2003-503365 | A | 1/2003 |
| JP | 2003-503395 | | 1/2003 |
| JP | 2003-528034 | | 9/2003 |
| WO | WO 89/06692 | | 7/1989 |
| WO | WO 93/21319 | | 10/1993 |
| WO | WO 94/00136 | | 1/1994 |
| WO | WO 94/22478 | | 10/1994 |
| WO | WO 96/16173 | | 5/1996 |
| WO | WO 97/00271 | | 1/1997 |
| WO | WO 97/04801 | | 2/1997 |
| WO | WO 98/02463 | | 1/1998 |
| WO | WO 98/08506 | | 3/1998 |
| WO | WO 98/08506 | A1 | 3/1998 |
| WO | WO 98/17797 | | 4/1998 |
| WO | WO 99/31140 | | 6/1999 |
| WO | WO 00/20579 | | 4/2000 |
| WO | WO 00/69460 | | 11/2000 |
| WO | WO 01/00238 | | 1/2001 |
| WO | WO 01/00244 | | 1/2001 |
| WO | WO 0100245 | | 1/2001 |
| WO | WO 0100594 | | 1/2001 |
| WO | WO 01/15730 | | 3/2001 |
| WO | WO 0124763 | | 4/2001 |
| WO | WO 02/16429 | | 2/2002 |
| WO | WO 03/000113 | | 1/2003 |
| WO | WO 03/024392 | | 3/2003 |
| WO | WO 03/070234 | | 8/2003 |
| WO | WO 2004/005470 | | 1/2004 |
| WO | WO 2004/016225 | | 2/2004 |

OTHER PUBLICATIONS

Epstein et al (International Journal of Cancer Supplement 8, 1994, pp. 57-59).*

Alpaugh et al (Clinical Cancer Research, 1998, vol. 4, pp. 1903-1914).*

Aasland et al., "Expression of oncogenes in thyroid tumours: Coexpression of c-*erbB*", *Br. J. Cancer*, 57:358-363 (1988).

Aoe et al., "Synergistic effect of docetaxel (DCT) and vinorelbine (VNB) against in vitro growth of a human small-cell lung cancer cell line", *Proceedings of the American Association for Cancer Research*, 37:375 (1996), Abstract No. 2560.

Apelgren et al., *Cancer Research*, 50:3540-3544 (1990).

Arteaga et al., "p185$^{c\text{-}erbB\text{-}2}$ signaling enhances cisplatin-induced cytotoxicity in human breast carcinoma cells: Association between an Oncogenic receptor tyrosine kinase and drug-induced DNA repair", *Cancer Research*, 54:3758-3765 (1994).

Bacus et al., "Differentiation of Cultured Human Breast Cancer Cells (AU-565 and MCF-7) Associated with Loss of Cell Surface *HER-2/neu* Antigen", *Molecular Carcinogenesis*, 3:350-362 (1990).

Bacus et al., "Tumor-Inhibitory monoclonals antibodies to the HER-2/Neu receiptor induce differentiation of Human breast cancer cells", *Cancer Research*, 52:2580-2589 (1992).

Bai et al., *Cancer Research*, 56:4398-4406 (1996).

Baselga et al., "Phase II Study of Weekly Intraveneous Recombinant Humanized Anti-p185$^{HER2}$ Monoclonal Antibody in Patients with HER2/*neu*-Overexpressing Metastatic Breast Cancer", *J. Clin. Oncol.*, 14:737-744 (1996).

Blakely et al., "An overview of therapy with immunotoxins containing ricin or its A-Chain", *Antigody Immunoconjugates, and Radiopharmaceutical*, 1(1):1-16 (1998).

Blättler et al., "Preclinical Immunotoxin Development", Basic and Clinical Oncology, pp. 1-22 (1998).

Borst et al., "Oncogene Alternations in Endometrial Carcinoma", *Gynecol. Oncol.*, 38:364-366 (1990).

Burris III, "Docetaxel (Taxotere) in HER-2-positive patients and in combination with Trastuzumab (Herceptin)", *Seminars in Oncology*, 27(No. 2, Suppl. 3):19-23 (2000).

Carlsson et al., "Protein Thiolation and Reversible Protein-Protein Conjugation N-Succinimidyl 3-(2- Pyridyldithio)Propionate, a New Heterobifunctional Reagent", *Biochemical Journal*, 173(3):723-737 (1978).

Carter et al., "Humanization of anti-p185$^{HER2}$ antibody for human cancer therapy", *Proc. Natl. Acad. Sci.*, USA, 89:4285-4289 (1992).

Chaemmaghami et al., "New Agents in the Treatment of Small Cell Lung Cancer", *Chest*, 113(1 Suppl):86S-91S (1998).

(56) References Cited

OTHER PUBLICATIONS

Chan et al., "Synergistic effects of doxorubicin and modulators of multidrug resistance in small cell lung cancer (SCLC) cells naturally expressing MDR-1, MRP and LRP phenotypes", *Proceedings Am. Assoc. for Cancer Res.*, 38:591-592 (1997).
Chari et al., "Dose-response of the anti-tumor effect of huN901-DM1 against human small-cell lung cancer xenografts", *Proceedings of the American Association for Cancer Research*, 41:693 (2000).
Chari, "Targeted Delivery of Chemotherapeutics: tumor-activated prodrug therapy", *Advanced Drug Delivery Reviews*, 31:89-104 (1998).
Chari, et al. "Immunoconjugates Containing Novel Maytainsinoids: Promising Anticancer Drugs", *Cancer Research* 52:127-131 (1992).
Chari, et al. "Enhancement of the Selectivity and Antitumor Efficacy of a cc-1065 Analogue through Immunoconjugate Formation", *Cancer Research* 55:4079-4084 (1995).
Christian et al., *Gynecologic Oncology*, 55:s143-s150 (1994).
Chou, T. C., et al., "Quantitative analysis of dose-effect relationships: the combined effects of multiple drugs or enzyme inhibitors", Advances in Enzyme Regulation, vol. 22, pp. 27-55, 1984.
Clark, "Protein Engineering of Antibody Molecules for Prophylatic and Therapeutic Applications in Man", pp. 4-5 (1993).
Cobleigh et al., "Multinational Study of the Efficacy and Safety of Humanized Anti-HER2 Monoclonal Antibody in Women who have HER2-Overexpressing Metastatic Breast Cancer that has progressed After Chemotherapy for Metastatic Disease", *J. Clin. Oncol.*, 17:2639-2648 (1999).
Cohen et al., "Expression pattern of the *neu* (NGL) gene-encoded growth factor protein ($p185^{neu}$) in normal and transformed epithelial tissues of the digestive tract", *Oncogene*, 4:81-88 (1989).
Mandler et al., "Synthethesis and Evaluation of Antiproliferative Activity of a Geldanamycin-herceptin Immunoconjugate", *Bioorganic and Medicinal Chem. Letters*, 10:1025-1028 (2000).
Decision of Rejection for JP 2007-284684 dated Feb. 23, 2012.
Dieras et al., 10th NCI-EORTC Symposium on New Drugs in Cancer Therapy, p. 100, Abstract Nos. 382 and 383 (Jun. 1998).
Doria et al., *Cancer*, 62:1939-1945 (1988).
Drebin et al., "Monoclonal antibodies reactive with distinct domains of the *neu* oncogene-encoded p185 molecule exert synergistic anti-tumor effects in vivo", Oncogene, 2:273-277 (1988).
Drebin et al., "Down-modulation of an Oncogene Protein Product and Reversion of the Transformed Phenotype by Monoclonal Antibodies", *Cell*, 41:695-706 (1985).
D'Souza et al., "Overexpression of ERBB2 in human mammary epithelial cells signals inhibition of transcription of the E-cadherin gene", *Proc. Natl. Acad. Sci., USA*, 91:7202-7206 (1994).
Embleton et al., *Br. J. Cancer*, 47:043-049 (1993).
Epstein et al., "Use of the Immunotoxin N901-Blocked Ricin in Patients with Small-Cell Lung Cancer", *Int. J. Cancer Suppl.*, 8:57-59 (1994).
Erickson et al., "Antibody-Maytansinoid Conjugates are activated in targeted cancer cells by Lysosomal degradation and Linker-Dependent Intracellular Processing", *Cancer Res.*, 66(8):4426-4433 (2006).
European Office Action dated Nov. 24, 2010, as issued in European Patent Application No. 00 970 516.1.
Partial European Search Report dated Jan. 20, 2011, issued in European Patent Application No. 10 18 5092 on Jan. 26, 2011.
European Search Report dated Jan. 20, 2011, issued in European Patent Application No. 10 18 5092 on May 16, 2011.
Examiner's Report issued in Australian Patent Application No. 2004282491 dated Aug. 21, 2009.
Fedier et al., *Annals of Oncology*, 14:938-945 (2003).
Fendly et al., "Characterization of murine monoclonal antibodies reactive to either the humnan epidermal growth factor receipt or HER2/neu gene product", *Cancer Research*, 50:1550-1558 (1990).
Fitzpatrick et al., *International Immunopharmacology*, 3: 1699-1714 (2003).
Fiorentino et al., *Dev. Oncol.*, 54:415-435 (1988), Abstract.
Fornier et al., "Update on the management of advanced breast cancer", *Oncology*, 13(5):647-658 (1999).
Fukushige et al., "Localization of a Novel v-erbB-Related Gene, c-erbB-2, on Human Chromosome 17 and its Amplification in a Gastric Cancer Cell Line", *Molecular and Cellular Biology*, 6(3):955-958 (1986).
Ghaemmaghami et al., *Chest*, 113(Supp. 1):86s-91s (1998).
Gianni et al., "Putting taxanes to work in operable breast cancer: a search for selective indications from empirical studies", *Recent Results in Cancer Research*, 152:314-322 (1998).
Glisson et al., *Journal of Clinical Oncology*, 17(8):2309-2315 (1999).
Griffin et al., *The Journal of Immunology*, 130(6):2947-2951 (1983).
Gu et al., "Synergistic effect of paclitaxel and 4-hydroxytamoxifen on estrogen receptor-negative colon cancer and lung cancer cell lines", *Anti-Cancer Research*, 10(10):895-901 (1999).
Gu et al., "Overexpression of her-2/*neu* in human prostate cancer and benign hyperplasia", *Cancer Letters*, 99:185-189 (1996).
Guchelaar et al., *Clinical Oncology*, 6:40-48 (1994), Abstract.
Guérin et al., "Overexpression of Either *c-myc* or c-*erbB-2/neu* Proto-Oncogenes in Human Breast Carcinomas: Correlation with Poor Prognosis", *Oncogene Reseach*, 3:21-31 (1988).
Gupta, "Cross-Resistance of Vinblastine and Taxol-Resistant Mutants of Chinese Hamster Ovary Cells to Other Anticancer Drugs." *Cancer Treatment Reports*, 69(5):515-521 (1985).
Hancock et al., "A monoclonal antibody against the c-erbB-2 protein enhances the cytotoxicity of cis-Diamminedichloroplatinum against human breast and ovarian tumor cell lines", 51:4575-4580 (1991).
Harweth et al., "Monoclonal Antibodies against the Extracellular Domain of the erbB-2 Receptor Function as Partial Ligand Agonists", *The Journal of Biological Chemistry*, 267(21):15160-15167 (1992).
Hortobagyi, "Docetaxel in breast cancer and a rationale for combination therapy", *Oncology*, 11(6):11-15 (1997).
Hortobagyi, "Recent progress in clinical development of doxetaxel (Taxotere)", *Seminars in Oncology*, 26(No. 3, Suppl. 9):32-36 (1999).
Hudziak et al., "$p185^{HER2}$ Monoclonal Antibodies has antiproliferative effects in vitro and sensitizes human Breast tumor cells to Tumor necrosis factor", *Molecular and Cellular Biology*, 9(3):1165-1172 (1989).
ImmunoGen, Inc., Press Release (Feb. 25, 1999).
Issell et al., "Mayatansine", *Cancer Treatment Reviews*, 5:199-207 (1978).
Iwasaki et al., *Yakugaku Zasshi*, 118:111-126 (1998), Abstract.
Jordan et al., "Tubulin as a Target for Anticancer Drugs: Agents Which Interact with the Mitotic Spindle." *Medicinal Research Reviews*, 18(4):259-296 (1998).
Kasprzyk et al., "Therapy of an animal model of human gastric cancer using a combination of anti-erbB-2 monoclonals antibodies", *Cancer Research*, 52:2771-2776 (1992).
Kaufman et al., "Utility of 123C3 monoclonal antibody against CD56 (NCAM) for the diagnosis of small cell carcinomas on paraffin sections", *Human Pathology*, 28(12):1373-1378 (1997).
Kawai et al., "Chemical Modification of Ansamitocins. III. Synthesis and Biological Effects of 3-Acyl Esters of Maytansinol,", *Chemical and Pharmaceutical Bulletin*, 32(9):3441-3451 (1984).
Kern et al., "p185neu expression in human lung adenocarinomas predicts shortened survival", *Cancer Research*, 50:5184-5191 (1990).
Kibbelaar et al., *Journal of Pathology*, 159:23-28 (1989).
King et al., "Amplification of a Novel v-erbB-Related Gene in a Human Mamary Carcinoma", *Science*, 229:974-976 (1985).
Klapper et al., "A subclass of tumor-inhibitory monoclonal antibodies to ErbB-2/HER2 blocks crosstalk With growth factor receptors", *Oncogene*, 14:2099-2109 (1997).
Kraus et al., "Isolation and characterization of *ERBB3*, a third member of the *ERBB I* epidermal growth Factor receptor family: Evidence for overexpression in a subset of human mammary tumors", *Proc. Natl. Acad. Sci.*, USA, 86:9193-9197 (1989).
Krek et al., "Expression and secretion of a recombinant ricin immunotoxin from murine myeloma cells", *Protein Engineering*, 8(5):481-489 (1995).

(56) References Cited

OTHER PUBLICATIONS

Kumar et al., "Regulation of Phosphorylation of the c-erbB-2/HER2 Gene Product by a Monoclonal Antibody and serum growth factor(s) in Human Mammary Carcinoma Cells", *Molecular and Cellular Biology*, 11((2):979-986 (1991).
Laguzza et al., *J. Med. Chem.*, 32:548-555 (1989).
Lewis et al., "Growth regulation of human breast and ovarian tumor cells by heregulin: Evidence for the requirement of ErbB2 as a critical component in mediating heregulin responsiveness", *Cancer Research*, 56:1457-1465 (1996).
Lewis et al., "Differential responses of human tumor cell lines to anti-p185$^{HER2}$ monoclonal antibodies", *Cancer Immunol. Immunother.*, 37:255-263 (1993).
Lidor et al., *Journal of Clinical Investigation*, 92:2440-2447 (1993).
Liu et al., "Eradication of large colon tumor xenografts by targeted delivery of maytansinoids", *Proc. Natl. Acad. Sci. USA*, 93:8618-8623 (1996a).
Liu et al., "Cure of human small cell lung cancer xenographs in scid mice by a HN901-maytansinoid immunoconjugate", *Proc. Annu. Meet. Am. Assoc. Cancer Res.*, 38(190):29 (1997a), Abstract No. 190.
Liu et al., "Cure of large human colon cancer xenografts by a C242-maystansinoid conjugate", *Proceedings of the American Association for Cancer Research*, 37(2):466-467 (1996b), Abstract No. 3183.
Liu et al., "The development of antibody delivery systems to target cancer with highly potent maystansinoids", *Exp. opin. Invest. Drugs*, 6(2):169-172 (1997b).
Lynch et al., "Immunotoxin therapy of small-cell lung cancer: a phase I study of N901-blocked ricin", *Journal of Clinical Oncology*, 15(2):723-734 (1997), Abstract.
Maier et al., "Requirements for the Internalization of a Murine Monoclonal Antibody directed against the Her-2/neu Gene Product c-erbB-2", *Cancer Research*, 51:5361-5369 (1991).
McCann et al., "*c-erbB-2* Oncoprotein Expression in Primary Human Tumors", *Cancer*, 65:89-92 (1990).
McKenzie et al., "Generation and characterization of monoclonal antibodies specific for the human *neu* Oncogene product, p185", *Oncogene*, 4:543-548 (1989).
Mendelsohn et al., *Clin. Cancer Res.*, 3:2703-2707 (1997).
Milas et al., "Enhancement of tumor radioresponse of a murine mammary carcinoma by paclitaxel", *Cancer Research*, 54(13):3506-3510 (1994).
Morikawa et al., "Pulmonary malignant fibrous histiocytoma treated with cisplatin plus etoposide followed by surgery", *Nihon Kyobu Shikkan Gakkai Zasshi, Japanese Journal of Thoracic Diseases*, 33(9):993-998 (1995), English Abstract.
Morris et al., *Journal of Clinical Oncology*, 16(3):1094-1098 (1998).
Myers et al., "Biological Effects of monoclonal Antireceptor Antibodies Reactive with *neu* Oncogene Product, p185*neu", Methods in Enzymology*, 198:277-290 (1991).
Nakajima et al., "Increase in the Chemically-Induced Differentiation of Human Leukemia Cell Lines by Tubulin Disruptors." *Biol. Pharm. Bull.*, 17(5):742-744 (1994).
Nguyen et al., "Synergistic tumoricidal effect of the paclitaxel and 17 allylamino geldanamycin (17AAG) combination in non-small cell lung cancer: in vitro and in vivo analysis", *Proceedings of the Am. Assoc. for Cancer Research*, 42:68-69 (2001).
Norton et al., "Overall survival (OS) advantage to simultaneous chemotherapy (CRx) plus the humanized anti-HER2 monoclonal antibody Herceptin (H) in HER2-overexpressing (HER2+)", *Proc. Annu. Meet. Am. Soc. Clin. Oncol.*, 18:A483 (1999).
Notice of Reasons for Rejection dated Oct. 27, 2010, for JP Patent Application No. 2007-284684, Communication.
Panda et al., *Proc. Natl. Acad. Sci. USA*, 95:9313-9318 (1998).
Park et al., "Amplification, Overexpression and rearrangement of the erbB-2 protooncogene in primary Human stomach carcinomas", *Cancer Research*, 49:6605-6609 (1989).
Pegram et al, *Oncogene*, 18:2241-2251 (1998).
Perez, "Current management of metastatic breast cancer", *Seminars in Oncology*, 26(No. 4, Suppl. 12):1-10 (1999a).
Perez, "Paclitaxel plus nonathracycline combinations in metastatic breast cancer, Seminars in Oncology", 26(No. 1, Suppl. 2):21-26 (1999b).
Pettit et al., *J. Am. Chem. Soc.*, 111:5463-5465 (1989).
Pietras et al., "Antibody to HER-2/*neu* receptor blocks DNA repair after cisplatin in human breast and Ovarian cancer cells", *Oncogene*, 9:1829-1838 (1994).
Pitot et al., *Clinical Cancer Research*, 5:525-531 (1999).
Plowman et al., "Heregluin incudes tyrosine phosphorylation of HER4/P180$^{ERBb4}$", *Letters to Nature*, 366:473-475 (1993a).
Plowman et al., "Ligand-specific activation of HER4/p180$^{ERBb4}$, a fourth member of the epidermal growth factor receptor family", *Proc. Natl. Acad. Sci., USA*, 90:1746-1750 (1993b).
Ranson et al., "Perspecitives on anti-HER monoclonal antibodies", *Oncology*, 63(suppl 1):17-21 (2002).
Roguska et al., "A comparison of two murine monoclonal antibodies humanized by CDR-grafting and variable domain resurfacing", *Protein Engineering*, 9(10):895-904 (1996).
Roguska et al., "Humanization of murine monoclonal antibodies through variable domain resurfacing", *Proceedings of the National Academy of Sciences USA*, 91(3):969-973 (1994).
Rosenblum et al., *Cancer Immunol. Immunother.*, 42:115-121 (1996).
Ross et al., "Prognostic Significance of HER-2/*neu* Gene Amplification Status by Fluorescence in Situ Hybridization of Prostate Carcinoma", *Cancer*, 79:2162-2170 (1997a).
Ross et al., "HER-2/*neu* Gene Amplification Status in Prostate Cancer by Fluorescence in Situ Hybridization", *Human Pathology*, 28(7):827-833 (1997b).
Roy et al., "Elimination of neuroblastoma and small-cell lung cancer cells with an anti-neural cell adhesion molecule immunotoxin", *Journal of the National Cancer Institute*, 88(16):1136-1145 (1996).
Rygaard et al., *Br. J. Cancer*, 65:573-577 (1992).
Sadasivan et al., "Overexpression of Her-2/NEU may be an indicator of Poor prognosis in Prostate Cancer", *The J. of Urology*, 150:126-131 (1993).
Sarup et al., "Characterization of an anti-p185HER2 monoclonal antibody that stimulates receptor function and inhibits tumor cell growth", *Growth Regulation*, 1:72-82 (1991).
Schaefer et al., "γ-Heregulin: a novel heregulin isoform that is an autocrine growth factor for the human breast cancer cell line, MDA-MB-175", *Oncogene*, 15:1385-1394 (1997).
Schlom, "Monoclonal Antibodies: They're More and Less Than You Think, In: Molecular Foundations of Oncology", Ed. S. Broder, pp. 95-134 (1991).
Schrappe et al., *Cancer Research*, 52:3838-3844 (1992).
Scott et al., "p185$^{HER2}$ Signal transduction in breast cancer cells", *The J. of Biological Chemistry*, 266(22):14300-14305 (1991).
Shawver et al., "Ligand-like effects induced by Anti-c-erbB2 antibodies do not correlate with and are not Required for growth inhibition of human carcinoma cells", *Cancer Research*, 54:1367-1373 (1994).
Shepard et al., "Monoclonal antibody therapy of human cancer: Taking the HER2 Protooncogene to the Clinic", *Journal of Clinical Immunology*, vol. 11, No. 3 (1991).
Siegall et al., *Proc. Annu. Meet. Am. Assoc. Cancer Res.*, 38:A185 (1997).
Skrepnik et al., "Effects of anti-erbB2 (HER-2/*neu*) recombinant oncotoxin AR209 on human non-small Cell lung carcinoma grown orthotopically in athymic nude mice", *Clinical Cancer Research*, 2:1851-1857 (1996).
Slamon et al., "Human breast cancer: Correlation of Relapse and Survival with amplification of the HER-2/*neu* Oncogene", *Science*, 235:177-182 (1987).
Slamon et al., "Studies of the HER-2/*neu* Proto-oncogene in human breast and ovarian cancer", *Science*, 244:707-712 (1989).
Sliwkowski et al., "Coexpression of *erbB2* and *erbB3* proteins reconstitutes a high affinity receptor for Heregulin", *The Jounal of Biological Chemistry*, 269(20):14661-14665 (1994).
Smith et al., *Cancer Research*, 54:3779-3784 (1994).
Souhami, *Thorax*, 47:53-56 (1992).
Spector et al., "Study of the Biological Effects of Lapatinib, a Reversible Inhibitor of ErbB1 and ErbB2 Tyrosine Kinases, on Tumor

(56) References Cited

OTHER PUBLICATIONS

Growth and Survival Pathways in Patients with Advanced Malignancies", *Journ. of Clin. Onc.*, 23(11):2502-2512 (2005).
Stancovski et al., "Mechanistic Aspects of the Opposing Effects of Monoclonal Antibodies to the ERBB2 Receptor on Tumor Growth", *Proc. Natl. Acad. Sci., USA*, 88:8691-8695 (1991).
Supplementary Partial European Search Report from EPA No. 00970516.1 (dated Jul. 12, 2004).
Tagliabue et al., "Selection of Monoclonal Antibodies which Induce Internalization and Phosphorylation of $p185^{HER2}$ and Growth Inhibition of Cells with HER2/NEU Gene Amplification", *Int. J. Cancer*, 7:933-937 (1991).
"Today's Drug Therapy" Nankodo Co., Ltd., Jun. 5, 1999, the second impression of the 21th edition, pp. 134 and 142-143 (1999 Edition).
Trail et al., "Enhanced antitumor activity of paclitaxel in combination with the anticarcinoma immunoconjugate BR96-doxorubicin", *Clinical Cancer Research*, 5(11):3632-3638 (1999).
Villalona-Calero, *Journal of Clinical Oncology*, 16(8):2770-2779 (1998).
Vitetta et al., "Monoclonal antibodies as againsts: An expanded role for their use in cancer therapy", *Cancer Reserch*, 54:5301-5309 (1994).
Vogel et al., "Monotherapy of metastatic breast cancer: a review of newer agents", *Oncologist*, 4(1):17-33 (1999).
Watson et al., *Proc. Annu. Meet. Am. Assoc. Cancer Res.*, 37:A2997 (1996).
Weiner et al., "Expression of the *neu* gene-encoded protein ($P185^{neu}$) in human non-small cell carcinomas of the lung", *Cancer Research*, 50:421-425 (1990).
Williams et al., "Expression of c-erbB-2 in Human Pancreatic Adenocarcinomas", *Pathobiology*, 59:46-52 (1991).
Worrell et al, "Effect of Linkage variation on Pharmacokinetics of ricin A Chain- Antibody conjugates In Normal Rats", *Anti-Cancer Drug Design*, 1(3):179-188 (1986).
Xu et al, *Clinical Cancer Research*, 3(9):1629-1634 (1997), Abstract.
Xu et al., "Antibody-Induced Growth Inhibition is Mediated Through Immunochemically and Functionally Distinct Epitopes on the Extracellular Domain of the c-erbB-2 (HER-2/neu) Gene Product", *Int. J. Cancer.*, 53:401-408 (1993).
Yeh et al., "Growth inhibitory action of brefeldin A with taxol and tiazofurin in human breast carcinoma cells", *Cancer Biochemistry Biophysics*, 15(1):11-17 (1995).
Yokota et al., "Amplification of c-erbB2 oncogene in human adenocarcinomas in vivo", *The Lancet*, 1:765-767 (1986).
Yonemura et al., "Evaluation of Immunoreactivity for erbB-2 protein as a marker of poor short term Prognosis in gastric cancer", *Cancer Research*, 51:1034-1038 (1991).
Zhau et al., "Amplification and Expression of the c-erb B--2/neu Proto-Oncogene in Human Bladder Cancer", Molecular Carcinogenesis, 3:254-257 (1990).
Notice of Reasons for Rejection for Japanese Patent Application No. 2011099295 dated Feb. 27, 2013 (with English Translation).
Yoshitake et al., "Conjugation of Glucose Oxidase from *Aspergillus niger* and Rabbit Antibodies Using N-Hydroxysuccinimide Ester of N-(4-Carboxycyclohexylmethyl)-Maleimide", Eur. J. Biochem., 101:395-399 (1979).

* cited by examiner

1a $COCH(CH_3)N(CH_3)COCH_3$

1b H

COMPOSITIONS AND METHODS FOR TREATING CANCER USING IMMUNOCONJUGATES AND CHEMOTHERAPEUTIC AGENTS

Matter enclosed in heavy brackets [ ] appears in the original patent but forms no part of this reissue specification; matter printed in italics indicates the additions made by reissue.

RELATED APPLICATIONS

[This application] *Notice: More than one reissue application has been filed for the reissue of U.S. Pat. No. 7,303,749, filed Sep. 29, 2000. The present application is a reissue continuation application of U.S. patent application Ser. No. 13/349,078, filed Jan. 12, 2012 (now RE 43899, issued Jan. 1, 2013), which is a reissue continuation of application Ser. No. 12/631,508, filed Dec. 4, 2009 (now abandoned), which is a reissue application of U.S. application Ser. No. 09/671,995, filed Sep. 29, 2000 (U.S. Pat. No. 7,303,749, issued Dec. 4, 2007), which* claims priority to U.S. Provisional Application No. 60/157,051, filed Oct. 1, 1999. *The entire disclosures of the aforementioned related applications and patents are hereby incorporated by reference in their entirety.*

FIELD OF THE INVENTION

The present invention is based on the discovery that the administration of at least one immunoconjugate and at least one chemotherapeutic agent provides an unexpectedly superior treatment for cancer. The present invention is directed to compositions comprising at least one immunoconjugate and at least one chemotherapeutic agent and to methods of treating cancer using a therapeutically effective amount of at least one immunoconjugate and at least one chemotherapeutic agent. The present invention is also directed to methods of modulating the growth of selected cell populations using a therapeutically effective amount of at least one chemotherapeutic agent and at least one immunoconjugate.

BACKGROUND OF THE INVENTION

Of all lung cancer cases diagnosed in the United States every year, 20-25% are small cell lung cancer (SCLC). Current treatments for small cell lung cancer include surgery, radiation treatment, and chemotherapeutic agents, such as paclitaxel or a combination of etoposide and cisplatin. Despite these treatment options, there is only a 1-5% survival rate after 5 years in patients who have clinically evident metastatic disease upon diagnosis. Glisson et al, Journal of Clinical Oncology, 17(8):2309-2315 (August 1999).

Pre-clinical studies reveal that small cell lung cancers can also be treated with an immunoconjugate comprising a monoclonal antibody and a maytansinoid. Liu et al, Proceedings of the American Association for Cancer Research, 38:29 (abstract 190) (1997). In this study, the maytansinoid was DM1, and the monoclonal antibody was humanized N901. Humanized monoclonal antibody N901 targets CD56, which is expressed on substantially all small cell lung cancers.

There is a need in the art for new and more effective methods for treating cancer. The present invention is directed to these, as well as other, important ends.

SUMMARY OF THE INVENTION

The present invention is based on the discovery that the use of at least one chemotherapeutic agent and at least one immunoconjugate produces unexpectedly superior results in the treatment of cancer.

The present invention describes methods of treating cancer in a patient in need thereof by administering to the patient a therapeutically effective amount of at least one chemotherapeutic agent and at least one immunoconjugate. The chemotherapeutic agent can be any known in the art including, for example, taxane compounds, compounds that act via taxane mechanisms, platinum compounds, epipodophyllotoxin compounds, camptothecin compounds, or any combination thereof. The immunoconjugate can comprise a cell binding agent and at least one therapeutic agent for killing selected cell populations. The cell binding agent is preferably a monoclonal antibody or a fragment thereof, and the therapeutic agent for killing selected cell populations is preferably an anti-mitotic agent, such as a maytansinoid, a Vinca alkaloid, a dolastatin, or a cryptophycin. In particularly preferred embodiments, the immunoconjugate comprises the maytansinoid DM1 and humanized N901 monoclonal antibody. The chemotherapeutic agent and immunoconjugate can be administered separately or as components of the same composition.

The present invention also describes methods of modulating the growth of selected cell populations, such as cancer cells, by administering a therapeutically effective amount of at least one chemotherapeutic agent and at least one immunoconjugate. The chemotherapeutic agent can be any known in the art including, for example, taxane compounds, compounds that act via taxane mechanisms, platinum compounds, epipodophyllotoxin compounds, camptothecin compounds, or any combination thereof. The immunoconjugate can comprise a cell binding agent and at least one therapeutic agent for killing selected cell populations. The cell binding agent is preferably a monoclonal antibody or a fragment thereof, and the therapeutic agent for killing selected cell populations is preferably an anti-mitotic agent, such as a maytansinoid, a Vinca alkaloid, a dolastatin, or a cryptophycin. In particularly preferred embodiments, the immunoconjugate comprises the maytansinoid DM1 and humanized N901 monoclonal antibody. The chemotherapeutic agent and immunoconjugate can be administered separately or as components of the same composition.

The present invention also describes compositions comprising at least one chemotherapeutic agent and at least one immunoconjugate. The chemotherapeutic agent can be any known in the art including, for example, taxane compounds, compounds that act via taxane mechanisms, platinum compounds, epipodophyllotoxin compounds, camptothecin compounds, or any combination thereof. The immunoconjugate can comprise a cell binding agent and at least one therapeutic agent for killing selected cell populations. The cell binding agent is preferably a monoclonal antibody or a fragment thereof, and the therapeutic agent for killing selected cell populations is preferably an anti-mitotic agent, such as a maytansinoid, a Vinca alkaloid, a dolastatin, or a cryptophycin. In particularly preferred embodiments, the immunoconjugate comprises the maytansinoid DM1 and humanized N901 monoclonal antibody. The composition can comprise a pharmaceutically acceptable carrier, excipient or diluent.

These and other aspects of the present invention are described in detail herein.

DETAILED DESCRIPTION OF THE INVENTION

Figure 1:
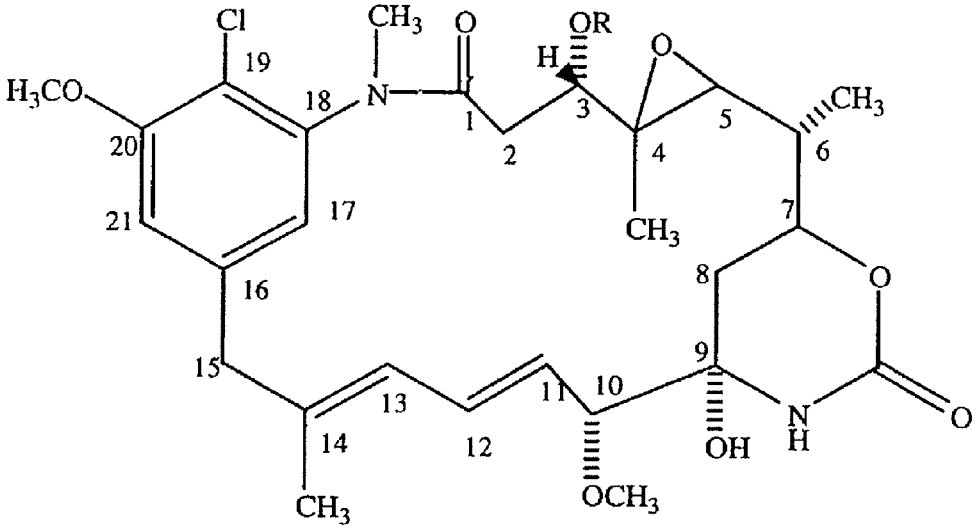
FIG. 1 shows maytansine (1a) and maytansinol (1b).
Figure 2:
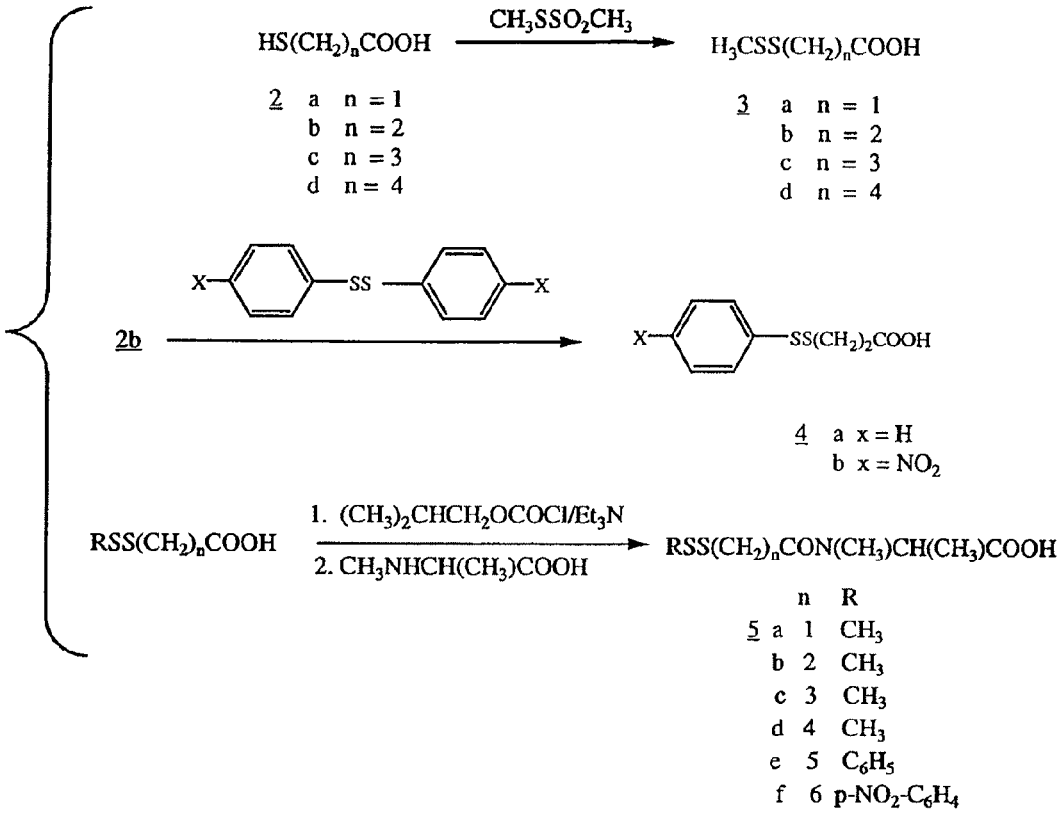
FIG. 2 shows the synthesis of disulfide-containing derivatives of N-methyl-L-alanine.
Figure 3:
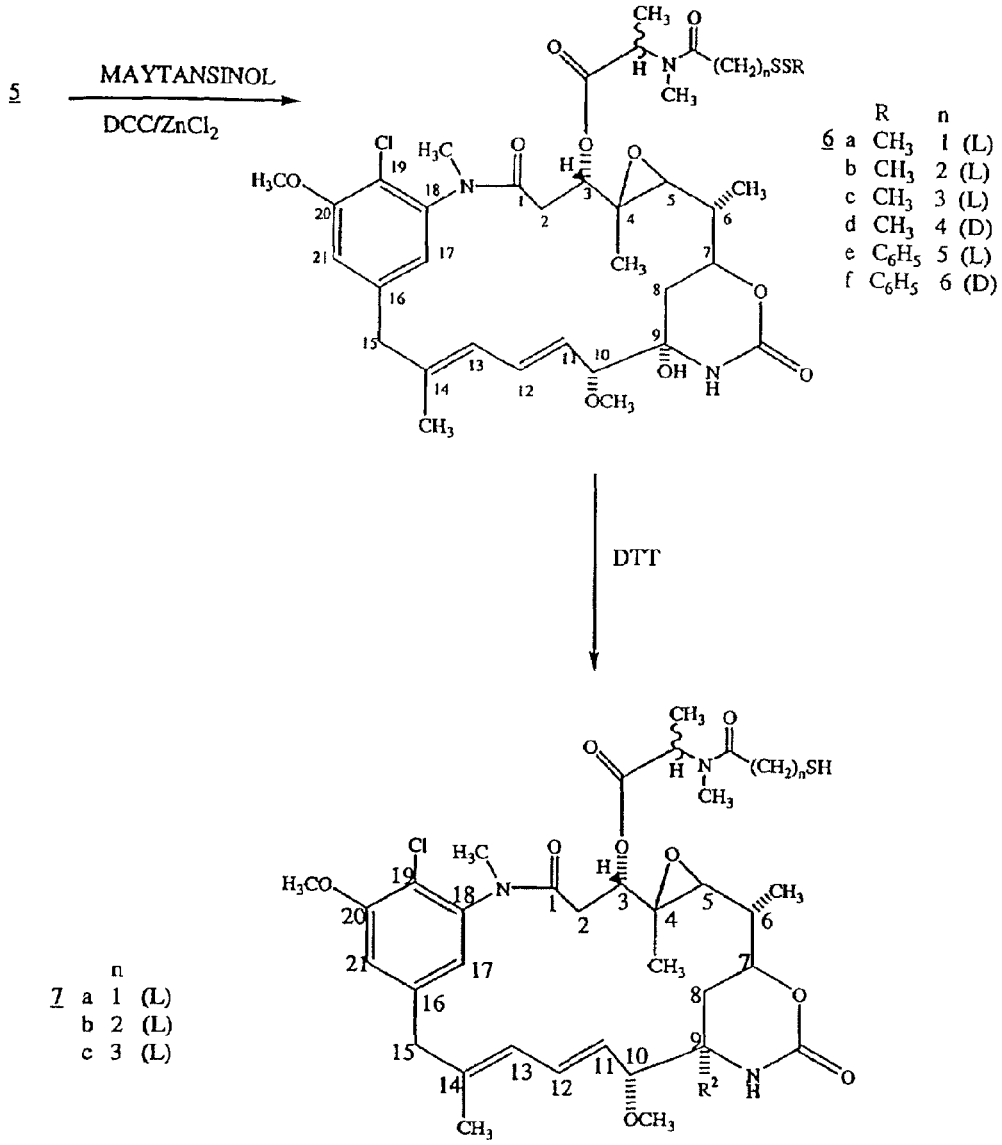
FIG. 3 shows the synthesis of disulfide- and thiol-containing maytansinoids which can be linked to cell binding agents via a disulfide or any other sulfur-containing link such as thioether or thioester links. The synthesis starts with the intermediates of FIG. 2.
Figure 4A:
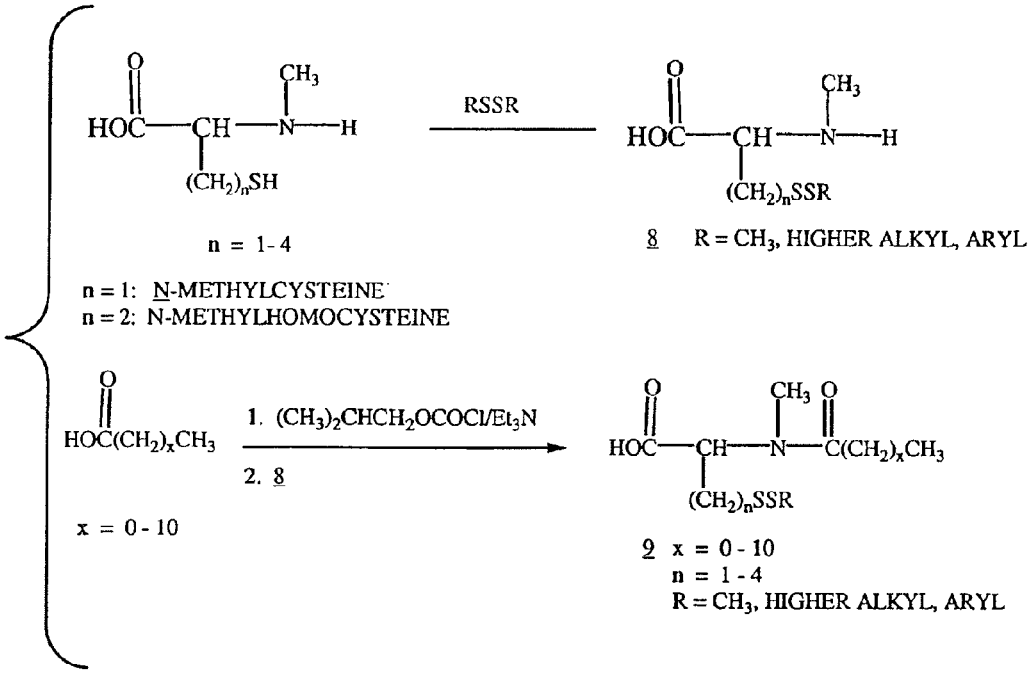
FIG. 4a shows the synthesis of disulfide- and thiol-containing derivatives of N-methyl-L-cysteine.
Figure 4B:
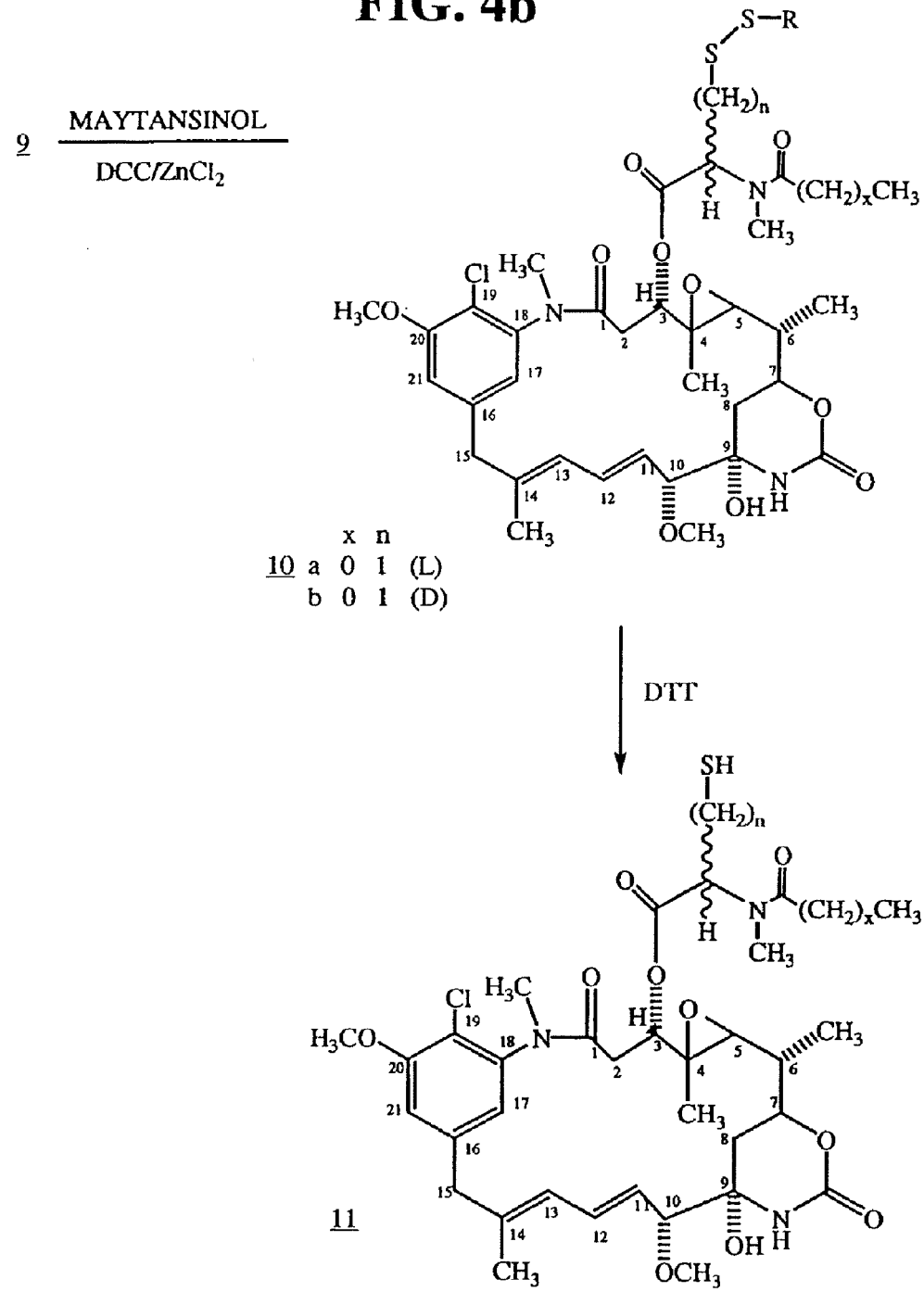
FIG. 4b shows the synthesis of disulfide- and thiol-containing maytansinoids from the intermediates of FIG. 4a that can be conjugated to cell binding agents via a disulfide or any other sulfur-containing link such as thioether or thioester links.

The present invention is based on the unexpected discovery that the administration of at least one chemotherapeutic agent and at least one immunoconjugate produces superior results in the treatment of cancer. Appropriate chemotherapeutic agents and immunoconjugates are described herein.

The immunoconjugates of the present invention comprise at least one therapeutic agent for killing selected cell populations linked to a cell binding agent. The therapeutic agent for killing selected cell populations is preferably an anti-mitotic agent. Anti-mitotic agents, which are known in the art, kill cells by inhibiting tubulin polymerization and, therefore, microtubule formation. Any anti-mitotic agent known in the art can be used in the present invention, including, for example, maytansinoids, Vinca alkaloids, dolastatins, cryptophycins, and/or any other agent that kills cells by inhibiting tubulin polymerization. Preferably, the anti-mitotic agent is a maytansinoid.

Maytansinoids that can be used in the present invention, to produce the modified maytansinoid capable of being linked to a cell binding agent, are well known in the art and can be isolated from natural sources according to known methods or prepared synthetically according to known methods. Preferred maytansinoids are those described, for example, in U.S. Pat. No. 5,208,020, the disclosure of which is incorporated by reference herein in its entirety.

Suitable maytansinoids include maytansinol and maytansinol analogues. Examples of suitable maytansinol analogues include those having a modified aromatic ring and those having modifications at other positions. Specific examples of suitable analogues of maytansinol having a modified aromatic ring include: C-19-dechloro (U.S. Pat. No. 4,256,746) (prepared by LAH reduction of ansamitocin P-2); C-20-hydroxy (or C-20-demethyl)+/−C-19-dechloro (U.S. Pat. Nos. 4,361,650 and 4,307,016) (prepared by demethylation using Streptomyces or Actinomyces or dechlorination using LAH); and C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include: C-9-SH (U.S. Pat. No. 4,424,219) (prepared by the reaction of maytansinol with $H_2S$ or $P_2S_5$); C-14-alkoxymethyl (demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol).

In order to link the maytansinoid to the cell binding agent, the maytansinoid must be modified, and a linking group can be used. Suitable linking groups are known in the art and include, for example, disulfide groups, thioether groups, acid labile groups, photolabile groups, peptidase labile groups and esterase labile groups. Preferred are disulfide groups and thioether groups.

The linking group is part of a chemical moiety that is covalently bound to the maytansinoid through conventional methods. In a preferred embodiment, the chemical moiety can be covalently bound to the maytansinoid via an ester linkage.

Many positions on maytansinoids are useful as the linkage position, depending upon the type of link. For example, for forming an ester linkage, the C-3 position having a hydroxyl group, the C-14 position modified with hydroxymethyl, the C-15 position modified with hydroxy, and the C-20 position having a hydroxy group are all expected to be useful. The C-3 position is preferred and the C-3 position of maytansinol is especially preferred. Also preferred is an N-methyl-alanine-containing C-3 ester and an N-methyl-cysteine-containing C-3 ester of maytansinol or its analogues.

The synthesis of esters of maytansinol having a linking group is described in U.S. Pat. No. 5,208,020. While the synthesis of esters of maytansinol having a linking group is described herein in terms of thiol and disulfide linking groups, one of skill in the art will understand that other linking groups can also be used with the invention, as can other maytansinoids.

The synthesis of maytansinoid derivatives can be described by reference to FIGS. 1, 2, 3, 4a and 4b, where disulfide-containing maytansinoid esters are prepared by condensing maytansinol 1b with freshly prepared N-methyl-L-alanine or N-methyl-L-cysteine derivatives containing a disulfide group.

ω-Mercapto-carboxylic acids of varying chain lengths are converted into their respective methyl-dithio, e.g., 3a-3d (where n=1-10, including branched and cyclic aliphatics), or aryl-dithio, e.g., 4a-4b, derivatives by reacting them with methyl methanethiolsulfonate or aryldisulfides, such as diphenyldisulfide and ring substituted diphenyldisulfides and heterocyclic disulfides such as 2,2-dithiopyridine. The carboxylic acids are activated and then reacted with N-methyl- L-alanine to form the desired carboxylic acid compounds, e.g., 5a-5f, for condensation with maytansinol 1b.

Esterification of maytansinol 1b or an analogue with the carboxylic acids 5a-5f gives the disulfide-containing maytansinoids 6a-6f. Cleavage of the disulfide group in 6a-6f with dithiothreitol gives the thiol-containing maytansinoids 7a-7c, which are readily linked via disulfide or thioether links to cell binding agents. N-methyl-L-alanine can be prepared as described in the literature (Fu et al, J. Amer. Chem. Soc., 75:1953); or is obtainable commercially (Sigma Chemical Company).

In another embodiment, N-methyl-cysteine or N-methyl-homocysteine can be converted to the respective disulfide derivatives 8 (n=1 and 2, respectively) which are then acylated to yield the desired carboxylic acids 9 (n=1 and 2, respectively). Maytansinol is then esterified with 9 (n=1) to give disulfide-containing ester 10. Reduction of 10a with dithiothreitol as described for 7b produces the thiol-containing maytansinoid 11 which can be conjugated to cell binding agents. N-methyl-cysteine can be prepared as described in Undheim et al, Acta Chem. Scand., 23:3129-3133 (1970).

More specifically, maytansinol 1b is derived from maytansine 1a or other esters of maytansinol by reduction such as with lithium aluminum hydride. (Kupchan et al, J. Med. Chem., 21:31-37 (1978); U.S. Pat. No. 4,360,462). It is also possible to isolate maytansinol from the microorganism Nocardia (U.S. Pat. No. 4,151,042). Maytansinol is then converted to the different ester derivatives, 6a to 6f and 10, using a suitable agent such as dicyclohexylcarbodiimide (DCC) and catalytic amounts of zinc chloride (U.S. Pat. Nos. 4,137,230 and 4,260,609; Kawai et al, Chem. Pharm. Bull., 32:3441-3951 (1984)). The two diastereomeric products containing the D and L-aminoacyl side chains result. The diastereomeric maytansinoid esters are readily separated by preparative TLC on silica gel. For example, using Analtech GF plates (1000 microns) and developing with 6% methanol in chloroform yields distinct banding: the desired bands are scraped off the plate and the products extracted with ethyl acetate (Kupchan, J. Med. Chem., 21:31-37 (1978) and U.S. Pat. No. 4,360,462).

Reduction of the disulfide-containing maytansinoids to the corresponding mercapto-maytansinoids 7a, 7b, 7c and 11, is achieved by treatment with dithiothreitol (DTT) and purification by HPLC using a Waters radialpak C-18 column and eluting with a linear gradient of 55% to 80% acetonitrile in $H_2O$ over 10 minutes at a flow rate of 1.5 ml/min.

When analogues of maytansinol are used as the starting material to give analogous disulfide-containing maytansinoid esters, the analogues are prepared before reacting them with the N-methyl-L-alanine or N-methyl-L-cysteine derivatives.

One example of N-methyl-alanine-containing maytansinoid derivatives useful in the present invention is represented by formula (I):

(I)

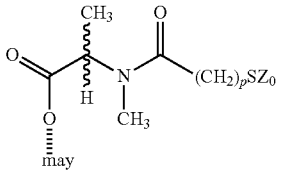

wherein $Z_0$ represents H or SR, wherein R represents methyl, linear alkyl, branched alkyl, cyclic alkyl, simple or substituted aryl or heterocyclic;

p represents an integer of 1 to 10; and

"may" represents a maytansinoid.

In a preferred embodiment of the compound of formula (I), $Z_0$ represents SR, R represents methyl, and p represents an integer of 2.

Another example of N-methyl-alanine-containing maytansinoid derivatives useful in the present invention is represented by formula (II):

(II)

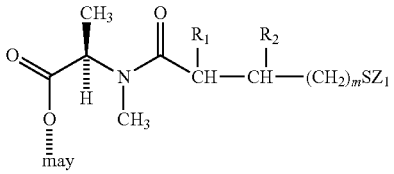

wherein $R_1$ and $R_2$, which may be the same or different, represents H, $CH_3$ or $CH_2CH_3$;

$Z_1$ represents H or $SR^3$, wherein $R^3$ represents methyl, linear alkyl, branched alkyl, cyclic alkyl, simple or substituted aryl, or heterocyclic:

m represents 0, 1, 2 or 3; and

"may" represents a maytansinoid.

Another example of N-methyl-alanine-containing maytansinoid derivatives useful in the present invention is represented by formula (III):

(III)

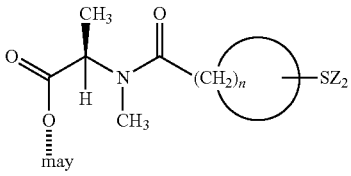

wherein:

$Z_2$ represents H or $SR_4$, wherein $R_4$ represents methyl, linear alkyl, branched alkyl cyclic alkyl, simple or substituted aryl, or heterocyclic;

n represents an integer of 3 to 8; and

"may" represents a maytansinoid.

Yet another example of N-methyl-alanine-containing maytansinoid derivatives useful in the present invention is represented by formula (IV):

(IV)

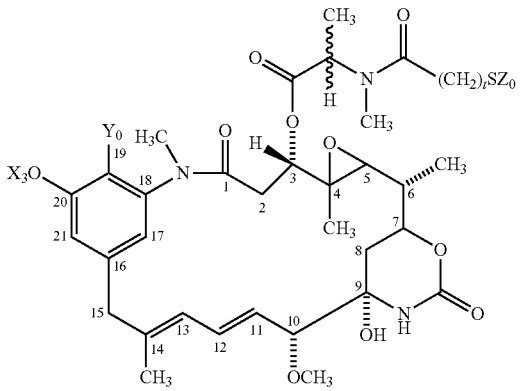

wherein:

$Z_0$ represents H or SR, wherein R represents methyl, linear alkyl, branched alkyl, cyclic alkyl, simple or substituted aryl or heterocyclic:

t represents 1, 2 or 3;

$Y_0$ represents Cl or H; and $X_3$ represents H or $CH_3$.

A specific example of N-methyl-cysteine-containing maytansinoid derivatives useful in the present invention is represented by formula (V):

(V)

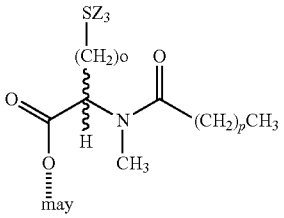

wherein:

$Z_3$ represents H or $SR_5$, wherein $R_5$ represents methyl, linear alkyl, branched alkyl, cyclic alkyl, simple or substituted aryl, or heterocyclic;

o represents 1, 2 or 3;

p represents 0 or an integer of 1 to 10; and

"may" represents a maytansinoid.

Another specific example of N-methyl-cysteine-containing maytansinoid derivatives useful in the present invention is represented by formula (VI):

(VI)

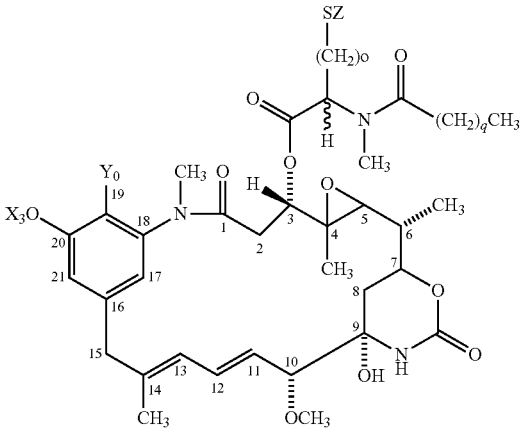

wherein:

$Z_3$ represents H or $SR_5$, wherein $R_5$ represents methyl, linear alkyl, branched alkyl, cyclic alkyl, simple or substituted aryl or heterocyclic;

o represents 1, 2, or 3;

q represents 0 or an integer of 1 to 10;

$Y_0$ represents Cl or H; and $X_3$ represents H or $CH_3$.

Examples of linear alkyls include methyl, ethyl, propyl, butyl, pentyl, and hexyl. Examples of branched alkyls include isopropyl, isobutyl, sec-butyl, tert-butyl, isopentyl, and 1-ethyl-propyl. Examples of cyclic alkyls include cyclopropyl, cyclobutyl, cyclopentyl, and cyclohexyl. Examples of simple aryls include phenyl, and naphthyl. Examples of substituted aryls include aryls such as those described above substituted with alkyl groups, with halogens, such as Cl, Br, F, nitro groups, amino groups, sulfonic acid groups, carboxylic acid groups, hydroxy groups, and alkoxy groups. Examples of heterocyclics are compounds wherein the heteroatoms are selected from O, N and S, and include pyrrollyl, pyridyl, furyl, and thiophene.

Vinca alkaloids that can be used in the present invention, to produce the modified Vinca alkaloids capable of being linked to a cell binding agent, are well known in the art. Such Vinca alkaloids include, for example, those described in Cancer Principles and Practice in Oncology, 4th Ed., DeVita et al, eds., J. B. Lippincott Company, Philadelphia Pa. (1993) and by Morris et al, J. Clin. Oncol., 16:1094-1098 (1998), the disclosures of which are incorporated herein by reference in their entirety. Exemplary Vinca alkaloids include vincristine, vinblastine, vindesine, navelbine (vinorelbine), and the like. Other Vinca alkaloids that can be used in the present invention include those described, for example, in U.S. Pat. Nos. 5,369,111, 4,952,408, 5,395,610, 4,522,750, 5,888,537, 5,891,724, 5,795,589, 4,172,077, 5,714,163, 5,436,243, 3,932,417, 5,869,620, 5,795,575, 5,780,446, 5,676,978, 5,604,237, 5,171,217, 4,831,038, 4,828,831, 4,765,972, 4,375,432, 4,309,415, 5,939,455, 5,874,402, 5,767,260, 5,763,733, 5,728,687, 5,716,928, 5,660,827, 5,541,232, 5,346,897, 5,220,016, 5,208,238, 5,190,949, 4,479,957, 4,160,767, 4,159,269, 4,096,148, RE 30,561, RE 30,560, U.S. Pat. Nos. 5,935,955, 5,922,340, 5,886,025, 5,866,679, 5,863,538, 5,855,866, 5,817,321, 5,783,178, 5,776,427, 5,767,110, 5,753,507, 5,723,625, 5,698,178, 5,686,578, 5,667,764, 5,654,287, 5,646,124, 5,635,515, 5,635,218, 5,606,017, 5,597,830, 5,595,756, 5,583,052, 5,561,136, 5,547,667, 5,543,152, 5,529,076, 5,491,285, 5,482,858, 5,455,161, 5,430,026, 5,403,574, 5,399,363, 5,397,784, 5,387,578, 5,364,843, 5,300,282, 5,182,368, 5,162,115, 5,147,294, 5,108,987, 5,100,881, 5,047,528, 5,030,620, 5,004,593, 4,946,833, 4,931,468, 4,923,876, 4,801,688, 4,737,586, 4,667,030, 4,617,305, 4,578,351, 4,476,026, 4,399,069, 4,279,817, 4,208,414, 4,199,504, 4,070,358, 4,029,663, 3,965,254, 3,954,773, 3,944,554, 3,887,565, 6,120,800, 6,071,947, 6,071,930, 6,069,146, 6,063,911, 5,994,367, 5,962,216, and 5,945,315, the disclosures of which are incorporated by reference herein in their entirety.

The Vinca alkaloids can be linked to cell binding agents, such as antibodies, via acid-labile hydrazide links by methods described by, for example, Laguzza et al, J. Med. Chem., 32:548-555 (1989), Schrappe et al, Cancer Res., 52:3838-3844 (1992), and Apelgren et al, Cancer Res., 50:3540-3544 (1990), the disclosures of which are incorporated by reference herein in their entirety. A preferable method is to link the Vinca alkaloids to a cell binding agent via disulfide bonds. The carboxy ester at the C-3 position of vinblastine, vincristine and navelbine can be hydrolzyed to the corresponding carboxylic acid using standard chemical methods. In vindesine, the carboxamide group at C-3 can be hydrolyzed to the free carboxy group. The free carboxy group in each of the Vinca alkaloids can be converted to an amide compound containing a terminal disulfide group by reaction with a protected cysteamine (e.g., methydithiocysteamine) in the presence of a coupling agent such as dicyclohexylcarbodidimide (DCC) or ethyl dimethylamin-propylcarbodiimide (EDC). The resulting disulfide containing Vinca alkaloid is reduced with a reducing agent, such as dithiothreitol, to provide a thiol-containing compound. The thiol-containing Vinca alkaloid can be coupled to a cell-binding agent via disulfide exchange as described herein for the preparation of antibody-maytansinoid conjugates.

Dolastatins that can be used in the present invention, to produce the modified dolastatins capable of being linked to a cell binding agent, are well known in the art. Such dolastatins include, for example, those described by Pitot et al, Clin. Cancer Res., 5:525-531 (1999) and Villalona-Calero et al, J. Clin. Oncol., 16:2770-2779 (1998), the disclosures of which are incorporated by reference herein in their entirety. Exemplary dolastatins include dolastatin 10, dolastatin 15, and the like. Other dolastatins that can be used in the present invention include those described, for example, in U.S. Pat. Nos. 5,945,543, 5,939,527, 5,886,147, 5,886,025, 5,883,120, 5,856,324, 5,840,699, 5,831,002, 5,821,222, 5,807,984, 5,780,588, 5,767,237, 5,750,713, 5,741,892, 5,665,860, 5,663,149, 5,654,399, 5,635,483, 5,626,864, 5,599,902, 5,554,725, 5,530,097, 5,521,284, 5,504,191, 5,502,032, 5,410,024, 5,410,024, 5,378,803, 5,352,804, 5,138,036, 5,091,368, 5,076,973, 4,986,988, 4,978,744, 4,879,278, 4,816,444, 4,486,414, 4,414,205, 6,103,913, 6,103,698, 6,096,757, 6,034,065, 6,020,495, 6,017,890, 6,004,934, 5,985,837, 5,965,700, and 5,965,537, the disclosures of which are incorporated by reference herein in their entirety.

The synthetic scheme described for dolastatin 10 by Pettit et al, J. Am. Chem. Soc., 111:5463-5465 (1989), the disclosure of which is incorporated by reference herein in its entirety, can be followed, with minor modification, to provide a thiol-containing dolastatin that can be linked via disulfide bonds to a cell binding agent, such as an antibody. The phenylalanine moiety in the dolphenine residue in the C-terminal of dolastatin 10 is replaced by a methyldithio-substituent containing amino acid. Thus, tyrosine can be converted into an ether by reaction with a commercially available dibromoalkane, such as 1,3-dibromobutane, using standard chemical methods. The resulting bromo compound is reacted with potassium thioacetate, followed by hydrolysis, to give a thiol-containing tyrosine. Conversion is achieved as described by Pettit, supra. The thiol-containing dolastatin can be coupled to a cell binding agent via disulfide exchange as described herein for the preparation of an antibody-maytansinoid conjugate.

Cryptophycins that can be used in the present invention, to produce the modified cryptophycins capable of being linked to a cell binding agent, are well known in the art. Such cryptophycins include, for example, those described by Smith et al, Cancer Res., 54:3779-3783 (1994), Panda et al, Proc. Natl. Acad. Sci., 95:9313-9318 (1998), and Bai et al, Cancer Res., 56:4398-4406 (1996), the disclosures of which are incorporated by reference herein in their entirety. Exemplary cryptophycins include cryptophycin 52, cryptophycin 1, and the like. Other cryptophycins that can be used in the present invention include those described, for example, in Great Britain Patent No. 2220657; European Patent Nos. 870506, 870501, 861838, 861839, 792875 and 870510; U.S. Pat. Nos. 6,103,913, 6,046,177, 6,020,512, 6,013,626, 5,977,387, 5,955,423, 5,952,298, 5,945,315, 5,886,025, and 5,833,994; and WIPO Publication Nos. 98/38178, 98/38164, 98/08829, 98/08506, 98/08505, 97/31632, 97/08334, 97/07798, 98/09601, 97/23211, 98/46581, 98/38158, 98/09988, 98/09974, 98/08812, and 98/09955, the disclosures of which are incorporated herein by reference in their entirety.

The aromatic methoxy group in the cryptophycins can be hydrolyzed by standard chemical or enzymatic methods to give the phenolic derivative. The phenol group can be converted into an ether by reaction with a commercially available dibromoalkane, such as 1,3-dibromobutane, using standard chemical methods. The resulting bromo compound is reacted with potassium thioacetate, followed by hydrolysis, to give a thiol-containing cryptophycin. The thiol-containing cryptophycin can be coupled to a cell binding agent via disulfide exchange as described herein for the preparation of antibody-maytansinoid conjugates.

Disulfide-containing and mercapto-containing maytansinoid (or Vinca alkaloid or dolastatin or cryptophycin) drugs of the invention can be evaluated for their ability to suppress proliferation of various unwanted cell lines using in vitro methods generally accepted in the art as being predictive of in vivo activity. For example, cell lines such as the human epidermoid carcinoma line KB, the human breast tumor line SKBR3 and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

The effectiveness of the immunoconjugates as therapeutic agents depends on the careful selection of an appropriate cell binding agent. Cell binding agents may be of any kind presently known, or that become known, and include peptides and non-peptides. Generally, these can be antibodies (especially monoclonal antibodies), lymphokines, hormones, growth factors, nutrient-transport molecules (such as transferrin), or any other cell binding molecule or substance.

More specific examples of cell binding agents that can be used include: monoclonal antibodies; fragments of antibodies such as Fv, Fab, Fab', and $F(ab')_2$ (Parham, J. Immunol., 131:2895-2902 (1983); Spring et al, J. Immunol., 113:470-478 (1974); Nisonoff et al, Arch. Biochem. Biophys., 89:230-244 (1960)); interferons (e.g., $\alpha$, $\beta$, $\gamma$); lymphokines such as IL2, IL3, IL-4, IL-6; hormones such as insulin, TRH (thyrotropin releasing hormone), MSH (melanocyte-stimulating hormone), steroid hormones such as androgens and estrogens; growth factors and colony-stimulating factors such as EGF, TGF-α, G-CSF, M-CSF and GM-CSF (Burgess, Immunology Today, 5:155-158 (1984)); and transferrin (O'Keefe et al, J. Biol. Chem., 260:932-937 (1985)).

Monoclonal antibody techniques allow for the production of extremely specific cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used.

Selection of the appropriate cell binding agent is a matter of choice that depends upon the particular cell population that is to be targeted, but in general monoclonal antibodies are preferred if an appropriate one is available.

For example, the monoclonal antibody J5 is a murine $IgG_{2a}$ antibody that is specific for the Common Acute Lymphoblastic Leukemia Antigen (CALLA) (Ritz et al, Nature, 283:583-585 (1980)) and can be used if the target cells express CALLA such as in the disease of acute lymphoblastic leukemia. Similarly, the monoclonal antibody anti-B4 is a murine $IgG_1$, that binds to the CD19 antigen on B cells (Nadler et al, J. Immunol., 131:244-250 (1983)) and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH which binds to melanocytes can be used for the treatment of melanoma.

Cancers of the breast and testes can be successfully targeted with estrogen (or estrogen analogues) or androgen (or androgen analogues), respectively, as cell binding agents.

In a preferred embodiment, the antibody or fragment thereof is one that is specific for lung cancer, preferably small cell lung cancer. An antibody or fragment thereof that is specific for small cell lung cancer can be determined by methods described in the art, such as by Doria et al, Cancer 62:1939-1945 (1988). Preferably, the antibody or fragment thereof binds to an epitope on the CD56 antigen, which is expressed on substantially all small cell lung cancers. For example, N901 is an IgG1 murine monoclonal antibody (also called anti-N901) that is reactive with CD56, which is expressed on tumors of neuroendocrine origin, such as small cell lung cancer. See Griffin et al, J. Immunol. 130:2947-2951 (1983), and Roguska et al, Proc. Natl. Acad. Sci. USA, 91:969-973 (1994), the disclosure of which are incorporated by reference herein in their entirety.

Preferred antibodies or fragments thereof that are specific for small cell lung cancers include, but are not limited to, N901, NKH-1, Leu-7, anti-Leu-7, and the like (Doria et al, Cancer 62:1939-1945 (1988); Kibbelaar et al, Journal of Pathology, 159:23-28 (1989)). Other suitable antibodies or fragments thereof for use in the present invention include, for example, S-L 3-5, S-L 4-20, S-L 7-3, S-L11-14, TFS-4, MOC-1, MOC-21, MOC-31, MOC-32, MOC-52, 123A8, 123C3, UJ13A, B10/B12, SWA4, SWA20, SWA21, SWA22, SWA23, LAM-8, 534F8, 703D4704A1 and SM1, which are further described in Table I of Chapter 3 of the Proceedings of the First International Workshop on Small Cell Lung Cancer Antigens (London 1987), published in Lung Cancer, 4:15-36 (1988), the disclosures of which are incorporated by reference herein in their entirety. In a most preferred embodiment, the antibody is N901, or a fragment thereof, that binds to an epitope on the CD56 antigen, such as Fv, Fab, Fab' and $F(ab')_2$. The monoclonal antibody or fragment thereof can be any other antibody that binds to the CD56 antigen with the same specificity as N901. "Same specificity" means that the antibody or fragment thereof can bind to the same antigen as demonstrated by a competitive binding assay with N901.

Another preferred antibody or fragment thereof that is useful in the present invention is C242 (commercially available from CanAg Diagnostics AB, Sweden). C242 is also described in U.S. Pat. No. 5,552,293, the disclosure of which is incorporated by reference herein in its entirety.

In other preferred embodiments, the antibodies described herein are humanized antibodies or fragments thereof because humanized antibodies or fragments thereof are not expected to elicit an immune response in humans. Generally, antibodies can be humanized through the application of different humanization technologies described, for example, in U.S. Pat. Nos. 5,225,539, 5,585,089, and 5,639,641, the disclosures of which are incorporated by reference herein in their entirety. The preparation of different versions of humanized N901, is described, for example, by Roguska et al Proc. Natl. Acad. Sci. USA, 91:969-973 (1994), and Roguska et al, Protein Eng., 9:895:904 (1996), the disclosures of which are incorporated by reference herein in their entirety. To denote a humanized antibody, the letters "hu" or "h" appear before the name of the antibody. For example, humanized N901 is also referred to as huN901 or hN901.

Conjugates of the maytansinoid derivatives of the invention and a cell binding agent can be formed using any techniques presently known or later developed. The maytansinoid ester can be modified to yield a free amino group and then linked to an antibody or other cell binding agent via an acid-labile linker, or a photolabile linker. The maytansinoid ester can be condensed with a peptide and subsequently linked to a cell binding agent to produce a peptidase-labile linker. The maytansinoid ester can be treated to yield a primary hydroxyl group, which can be succinylated and linked to a cell binding agent to produce a conjugate that can be cleaved by intracellular esterases to liberate free drug. Most preferably, the maytansinoid esters are treated to create a free or protected thiol group, and then one or many disulfide or thiol-containing maytansinoid derivatives are covalently linked to the cell binding agent via disulfide bond(s).

Representational conjugates of the invention are antibody/maytansinoid derivatives, antibody fragment/maytansinoid derivatives, epidermal growth factor (EGF)/maytansinoid derivatives, melanocyte stimulating hormone (MSH)/maytansinoid derivatives, thyroid stimulating hormone (TSH)/maytansinoid derivatives, estrogen/maytansinoid derivatives, estrogen analogue/maytansinoid derivatives, androgen/maytansinoid derivatives, androgen analogue/maytansinoid derivatives.

Maytansinoid conjugates of antibodies, antibody fragments, protein hormones, protein growth factors and other proteins are made in the same way. For example, peptides and antibodies can be modified with crosslinking reagents such as N-succinimidyl 3-(2-pyridyldithio)propionate, N-succinimidyl 4-(2-pyridyldithio)-pentanoate (SPP), 4-succinimidyloxycarbonyl-α-methyl-α-(2-pyridyldithio) toluene (SMPT), N-succinimidyl-3-(2-pyridyldithio)-butyrate (SDPB), 2-iminothiolane, or acetylsuccinic anhydride by known methods (U.S. Pat. No. 4,563,304; Carlsson et al, Biochem. J., 173:723-737 (1978); Blättler et al, Biochem., 24:1517-1524

(1985); Lambert et al, Biochem., 22:3913-3920 (1983); Klotz et al, Arch. Biochem. Biophys., 96:605 (1962); and Liu et al, Biochem., 18:690 (1979), Blakey and Thorpe, Antibody, Immunoconjugates and Radiopharmaceuticals, 1:1-16 (1988); Worrell et al, Anti-Cancer Drug Design, 1:179-184 (1986), the disclosures of which are incorporated by reference herein in their entirety). The cell binding agent containing free or protected thiol groups thus-derived is then reacted with a disulfide- or thiol-containing maytansinoid to produce conjugates. The conjugates can be purified by HPLC or by gel filtration.

Similarly, for example, estrogen and androgen cell binding agents, such as estradiol and androstenediol, can be esterified at the C-17 hydroxy group with an appropriate disulfide-containing carboxylic acid, e.g., dicyclohexylcarbodiimide, as a condensing agent. Examples of such carboxylic acids that can be used are 3-(2-pyridyldithio)propanoic acid, 3-methyldithiopropanoic acid, 3-phenyldithio-propanoic acid, and 4-(2-pyridyldithio)pentanoic acid. Esterification of the C-17 hydroxy group can also be achieved by reaction with an appropriately protected thiol group-containing carboxylic acid chloride, such as 3S-acetylpropanoyl chloride. Other methods of esterification can also be used as described in the literature (Haslam, Tetrahedron, 36:2400-2433 (1980)). The protected or free thiol-containing androgen or estrogen can then be reacted with a disulfide or thiol-containing maytansinoid to produce conjugates. The conjugates can be purified by column chromatography on silica gel or by HPLC.

Preferably monoclonal antibody or cell binding agent/maytansinoid conjugates are those that are joined via a disulfide bond, as discussed above, that are capable of delivering maytansinoid molecules. Such cell binding conjugates are prepared by known methods such as modifying monoclonal antibodies with succinimidyl pyridyl-dithiopropionate (SPDP) or SPP (Carlsson et al, Biochem. J., 173: 723-737 (1978)). The resulting thiopyridyl group is then displaced by treatment with thiol-containing maytansinoids to produce disulfide linked conjugates. Alternatively, in the case of the aryldithio-maytansinoids, the formation of the cell binding conjugate is effected by direct displacement of the aryl-thiol of the maytansinoid by sulfhydryl groups previously introduced into antibody molecules. Conjugates containing 1 to 10 maytansinoid drugs linked via a disulfide bridge are readily prepared by either method.

More specifically, a solution of the dithiopyridyl modified antibody at a concentration of 2.5 mg/ml in 0.05 M potassium phosphate buffer and 0.05 M sodium chloride, at pH 6.5 containing 2 mM EDTA is treated with the thiol-containing maytansinoid (1.7 molar equivalent/dithiopyridyl group). The release of pyridine-2-thione from the modified antibody is monitored spectrophotometrically at 343 nm. The reaction is allowed to proceed up to 18 hours. The antibody-maytansinoid conjugate is purified and freed of unreacted drug and other low molecular weight material by gel filtration through a column of Sephacryl S-300. The number of maytansinoids bound per antibody molecule can be determined by measuring the ratio of the absorbance at 252 nm and 280 nm. An average of 1-10 maytansinoid molecules/antibody molecule can be linked via disulfide bonds by this method.

Antibody-maytansinoid conjugates with non-cleavable links can also be prepared. The antibody can be modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephacryl S-300 column.

The modified antibodies are treated with the thiol-containing maytansinoid (1.25 molar equivalent/maleimido group). The mixtures are incubated overnight at about 4° C. The antibody-maytansinoid conjugates are purified by gel filtration through a Sephadex G-25 column. Typically, an average of 1-10 maytansinoids per antibody are linked.

A preferred method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result.

As described herein, the present invention is based on the unexpected discovery that the use of at least one immunoconjugate and at least one chemotherapeutic agent produces superior results in treating cancer. Any chemotherapeutic agent known in the art can be used in combination with the immunoconjugate of the present invention to achieve the unexpectedly superior results described and demonstrated herein. Preferably, the chemotherapeutic agent is a taxane compound, a compound that acts via a taxane mechanism, a platinum compound, an epidophyllotoxin compound, a camptothecin compound, and/or any combination thereof. As is known in the art, platinum compounds and epidophyllotoxin compounds are generally used together for treating cancer.

In one embodiment, the present invention provides methods of treating cancer and/or modulating the growth of selected cell populations (e.g., cancer cells) by administering at least one immunoconjugate and at least one taxane compound. In another embodiment, the present invention provides methods of treating cancer and/or modulating the growth of selected cell populations (e.g., cancer cells) by administering at least one immunoconjugate and at least one compound that acts via a taxane mechanism. In another embodiment, the present invention provides methods of treating cancer and/or modulating the growth of selected cell populations (e.g., cancer cells) by administering at least one immunoconjugate, and at least one platinum compound. In another embodiment, the present invention provides methods of treating cancer and/or modulating the growth of selected cell populations (e.g., cancer cells) by administering at least one immunoconjugate, at least one platinum compound, and at least one epidophyllotoxin compound. In another embodiment, the present invention provides methods of treating cancer and/or modulating the growth of selected cell populations (e.g., cancer cells) by administering at least one immunoconjugate and at least one camptothecin compound. In another embodiment, the present invention provides methods of treating cancer and/or modulating the growth of selected cell populations (e.g., cancer cells) by administering at least one immunoconjugate and at least one compound that is capable of inhibiting DNA topoisomerase I. In yet another embodiment, the present invention provides methods of treating cancer and/or modulating the growth of selected cell populations (e.g., cancer cells) by administering at least one immunoconjugate, at least one taxane compound, and at least one platinum compound. In yet another embodiment, the present invention provides methods of treating cancer and/or modulating the growth of selected cell populations (e.g., cancer cells) by administering at least one immunoconjugate, at least one taxane compound, at least one platinum compound, and, optionally, at least one epidophyllotoxin compound. In yet another embodiment, the present invention provides methods of treating cancer and/or modulating the growth of selected cell populations (e.g., cancer cells) by administering at least one immunoconjugate, at least one camptothecin compound, at least one platinum compound and, optionally, at least one epidophyllotoxin compound. In yet another embodiment, the present invention provides methods of treating cancer and/or modulating the growth of selected cell populations (e.g., cancer cells) by administering at least one immunoconjugate, at least one compound that acts via a taxane mechanism and at least one camptothecin compound. One skilled in the art will appreciate that the methods described in the present invention encompass administering at least one immunoconjugate with one or more chemotherapeutic agents selected from the group consisting of taxane compounds, compounds that act through a taxane mechanism, platinum compounds, epidophyllotoxin compounds, camptothecin compounds and compounds that can inhibit DNA topoisomerase I. In the methods of the present invention, the immunoconjugate and chemotherapeutic agent can be administered simultaneously, about the same time, or at different times, or can be components of a single composition.

Taxane compounds prevent the growth of cancer cells by affecting cell structures called microtubules, which play an important role in cell functions. In normal cell growth, microtubules are formed when a cell starts dividing. Once the cell stops dividing, the microtubules are broken down or destroyed. Taxane compounds stop the microtubules from breaking down, such that the cancer cells become clogged with microtubules so that they cannot grow and divide.

Taxane compounds are known in the art and include, for example, paclitaxel (available as TAXOL® from Bristol-Myers Squibb, Princeton, N.J.), docetaxel (available as TAXOTERE® from Aventis), and the like. Other taxane compounds that become approved by the U.S. Food and Drug Administration (FDA) or foreign counterparts thereof are also preferred for use in the methods and compositions of the present invention. Other taxane compounds that can be used in the present invention include those described, for example, in 10th NCI-EORTC Symposium on New Drugs in Cancer Therapy, Amsterdam, page 100, Nos. 382 and 383 (Jun. 16-19, 1998); and U.S. Pat. Nos. 4,814,470, 5,721,268, 5,714,513, 5,739,362, 5,728,850, 5,728,725, 5,710,287, 5,637,484, 5,629,433, 5,580,899, 5,549,830, 5,523,219, 5,281,727, 5,939,567, 5,703,117, 5,480,639, 5,250,683, 5,700,669, 5,665,576, 5,618,538, 5,279,953, 5,243,045, 5,654,447, 5,527,702, 5,415,869, 5,279,949, 5,739,016, 5,698,582, 5,478,736, 5,227,400, 5,516,676, 5,489,601, 5,908,759, 5,760,251, 5,578,739, 5,547,981, 5,547,866, 5,344,775, 5,338,872, 5,717,115, 5,620,875, 5,284,865, 5,284,864, 5,254,703, 5,202,448, 5,723,634, 5,654,448, 5,466,834, 5,430,160, 5,407,816, 5,283,253, 5,719,177, 5,670,663, 5,616,330, 5,561,055, 5,449,790, 5,405,972, 5,380,916, 5,912,263, 8,808,113, 5,703,247, 5,618,952, 5,367,086, 5,200,534, 5,763,628, 5,705,508, 5,622,986, 5,476,954, 5,475,120, 5,412,116, 5,916,783, 5,879,929, 5,861,515, 5,795,909, 5,760,252, 5,637,732, 5,614,645, 5,599,820, 5,310,672, RE 34,277, U.S. Pat. Nos. 5,877,205, 5,808,102, 5,766,635, 5,760,219, 5,750,561, 5,637,723, 5,475,011, 5,256,801, 5,900,367, 5,869,680, 5,728,687, 5,565,478, 5,411,984, 5,334,732, 5,919,815, 5,912,264, 5,773,464, 5,670,673, 5,635,531, 5,508,447, 5,919,816, 5,908,835, 5,902,822, 5,880,131, 5,861,302, 5,850,032, 5,824,701, 5,817,867, 5,811,292, 5,763,477, 5,756,776, 5,686,623, 5,646,176, 5,621,121, 5,616,739, 5,602,272, 5,587,489, 5,567,614, 5,498,738, 5,438,072, 5,403,858, 5,356,928, 5,274,137, 5,019,504, 5,917,062, 5,892,063, 5,840,930, 5,840,900, 5,821,263, 5,756,301, 5,750,738, 5,750,562, 5,726,318, 5,714,512, 5,686,298, 5,684,168, 5,681,970, 5,679,807, 5,648,505, 5,641,803, 5,606,083, 5,599,942, 5,420,337, 5,407,674, 5,399,726, 5,322,779, 4,924,011, 5,939,566, 5,939,561, 5,935,955, 5,919,455, 5,854,278, 5,854,178, 5,840,929, 5,840,748, 5,821,363, 5,817,321, 5,814,658, 5,807,888, 5,792,877, 5,780,653, 5,770,745, 5,767,282, 5,739,359, 5,726,346, 5,717,103, 5,710,099, 5,698,712, 5,683,715, 5,677,462, 5,670,653, 5,665,761, 5,654,328, 5,643,575, 5,621,001, 5,608,102, 5,606,068, 5,587,493, 5,580,998, 5,580,997, 5,576,450, 5,574,156, 5,571,917, 5,556,878, 5,550,261, 5,539,103, 5,532,388, 5,470,866, 5,453,520, 5,384,399, 5,364,947, 5,350,866, 5,336,684, 5,296,506, 5,290,957, 5,274,124, 5,264,591, 5,250,722, 5,229,526, 5,175,315, 5,136,060, 5,015,744, 4,924,012, 6,118,011, 6,114,365, 6,107,332, 6,072,060, 6,066,749, 6,066,747, 6,051,724, 6,051,600, 6,048,990, 6,040,330, 6,030,818, 6,028,205, 6,025,516, 6,025,385, 6,018,073, 6,017,935, 6,011,056, 6,005,138, 6,005,138, 6,005,120, 6,002,023, 5,998,656, 5,994,576, 5,981,564, 5,977,386, 5,977,163, 5,965,739, 5,955,489, 5,939,567, 5,939,566, 5,919,815, 5,912,264, 5,912,263, 5,908,835, and 5,902,822, the disclosures of which are incorporated by reference herein in their entirety.

Other compounds that can be used in the invention are those that act through a taxane mechanism. Compounds that act through a taxane mechanism include compounds that have the ability to exert microtubule-stabilizing effects and cytotoxic activity against rapidly proliferating cells, such as tumor cells or other hyperproliferative cellular diseases. Such compounds include, for example, epothilone compounds, such as, for example, epothilone A, B, C, D, E and F, and derivatives thereof. Other compounds that act through a taxane mechanism (e.g., epothilone compounds) that become approved by the FDA or foreign counterparts thereof are also preferred for use in the methods and compositions of the present invention. Epothilone compounds and derivatives thereof are known in the art and are described, for example, in U.S. Pat. Nos. 6,121,029, 6,117,659, 6,096,757, 6,043,372, 5,969,145, and 5,886,026; and WO 97/19086, WO 98/08849, WO 98/22461, WO 98/25929, WO 98/38192, WO 99/01124, WO 99/02514, WO 99/03848, WO 99/07692, WO 99/27890, and WO 99/28324, the disclosures of which are incorporated herein by reference in their entirety.

Other compounds that can be used in the invention include platinum compounds such as, for example, cisplatin (available as PLATINOL® from Bristol-Myers Squibb, Princeton, N.J.), carboplatin (available as PARAPLATIN® from Bristol-Myers Squibb, Princeton, N.J.), oxaliplatin (available as ELOXATINE® from Sanofi, France), iproplatin, ormaplatin, tetraplatin, and the like. Other platinum compounds that become approved by the FDA or foreign counterparts thereof are also preferred for use in the methods and compositions of the present invention. Platinum compounds that are useful in treating cancer are known in the art and are described, for example in U.S. Pat. Nos. 4,994,591, 4,906,646, 5,902,610, 5,053,226, 5,789,000, 5,871,710, 5,561,042, 5,604,095, 5,849,790, 5,705,334, 4,863,902, 4,767,611, 5,670,621, 5,384,127, 5,084,002, 4,937,262, 5,882,941, 5,879,917, 5,434,256, 5,393,909, 5,117,022, 5,041,578, 5,843,475, 5,633,243, 5,178,876, 5,866,169, 5,846,725, 5,646,011, 5,527,905, 5,844,001, 5,832,931, 5,676,978, 5,604,112, 5,562,925, 5,541,232, 5,426,203, 5,288,887, 5,041,581, 5,002,755, 4,946,954, 4,921,963, 4,895,936, 4,686,104, 4,594,238, 4,581,224, 4,250,189, 5,829,448, 5,690,905, 5,665,771, 5,648,384, 5,633,016, 5,460,785, 5,395,947, 5,256,653, 5,132,323, 5,130,308, 5,106,974, 5,059,591, 5,026,694, 4,992,553, 4,956,459, 4,956,454, 4,952,676, 4,895,935, 4,892,735, 4,843,161, 4,760,156, 4,739,087, 4,720,504, 4,544,759, 4,515,954, 4,466,924, 4,462,998, 4,457,926, 4,428,943, 4,325,950, 4,291,027, 4,291,023, 4,284,579, 4,271,085, 4,234,500, 4,234,499, 4,200,583, 4,175,133, 4,169,846, 5,922,741, 5,922,674, 5,922,302, 5,919,126, 5,910,102, 5,876,693, 5,871,923, 5,866,617, 5,866,615, 5,866,593, 5,864,024, 5,861,139, 5,859,034, 5,855,867, 5,855,748, 5,849,770, 5,843,993, 5,824,664, 5,821,453, 5,811,119, 5,798,373, 5,786,354, 5,780,478, 5,780,477, 5,776,925, 5,770,593, 5,770,222, 5,747,534, 5,739,144, 5,738,838, 5,736,156, 5,736,119, 5,723,460, 5,697,902, 5,693,659, 5,688,773, 5,674,880, 5,670,627, 5,665,343, 5,654,287, 5,648,362, 5,646,124, 5,641,627, 5,635,218, 5,633,257, 5,632,982, 5,622,977, 5,622,686, 5,618,393, 5,616,613, 5,612,019, 5,608,070, 5,595,878, 5,585,112, 5,580,888, 5,580,575, 5,578,590, 5,575,749, 5,573,761, 5,571,153, 5,563,132, 5,561,136, 5,556,609, 5,552,156, 5,547,982, 5,542,935, 5,525,338, 5,519,155, 5,498,227, 5,491,147, 5,482,698, 5,469,854, 5,455,270, 5,443,816, 5,415,869, 5,409,915, 5,409,893, 5,409,677, 5,399,694, 5,399,363, 5,380,897, 5,340,565, 5,324,591, 5,318,962, 5,302,587, 5,292,497, 5,272,056, 5,258,376, 5,238,955, 5,237,064, 5,213,788, 5,204,107, 5,194,645, 5,182,368, 5,130,145, 5,116,831, 5,106,858, 5,100,877, 5,087,712, 5,087,618, 5,078,137, 5,057,302, 5,049,396, 5,034,552, 5,028,726, 5,011,846, 5,010,103, 4,985,416, 4,970,324, 4,936,465, 4,931,553, 4,927,966, 4,912,072, 4,906,755, 4,897,384, 4,880,832, 4,871,528, 4,822,892, 4,783,452, 4,767,874, 4,760,155, 4,687,780, 4,671,958, 4,665,210, 4,645,661, 4,599,352, 4,594,418, 4,593,034, 4,587,331, 4,575,550, 4,562,275, 4,550,169, 4,482,569, 4,431,666, 4,419,351, 4,407,300, 4,394,319, 4,335,087, 4,329,299, 4,322,391, 4,302,446, 4,287,187, 4,278,660, 4,273,755, 4,255,417, 4,255,347, 4,248,840, 4,225,529, 4,207,416, 4,203,912, 4,177,263, 4,151,185, 4,140,707, 4,137,248, 4,115,418, 4,079,121, 4,075,307, 3,983,118, 3,870,719, RE 33,071, U.S. Pat. Nos. 6,087,392, 6,077,864, 5,998,648, and 5,902,610, the disclosures of which are incorporated by reference herein in their entirety.

As is known in the art, platinum compounds are preferably used in combination with at least one epipodophyllotoxin compound, including, for example, etoposide (also known as VP-16) (available as VEPESID® from Bristol-Myers Squibb, Princeton, N.J.), teniposide (also known as VM-26) (available as VUMON® from Bristol-Myers Squibb, Princeton, N.J.), and the like. Other epipodophyllotoxin compounds that become approved by the FDA or foreign counterparts thereof are also preferred for use in the methods and compositions of the present invention. Other epipodophyllotoxin compounds that can be used in the present invention include those described, for example, in U.S. Pat. Nos. 3,524,844, 5,643,885, 5,066,645, 5,081,234, 5,891,724, 5,489,698, 5,821,348, 5,571,914, 4,997,931, 4,547,567, 5,536,847, 5,326,753, 5,120,862, 5,011,948, 4,895,727, 4,795,819, 4,644,072, 5,688,926, 5,676,978, 5,660,827, 5,395,610, 5,346,897, 5,208,238, 5,190,949, 5,086,182, 4,965,348, 4,958,010, 4,874,851, 4,866,189, 4,853,467, 4,728,740, 4,716,221, 5,935,955, 5,863,538, 5,855,866, 5,776,427, 5,747,520, 5,739,114, 5,622,960, 5,606,060, 5,605,826, 5,541,223, 5,459,248, 5,455,161, 5,364,843, 5,300,500, 5,041,424, 5,036,055, 5,034,380, 4,935,504, 4,916,217, 4,912,204, 4,904,768, 4,900,814, 4,888,419, 4,567,253, RE 35,524, U.S. Pat. Nos. 6,107,284, 6,063,801, and 6,051,230, the disclosures of which are incorporated herein by reference in their entirety.

Other compounds that can be used in the present invention include camptothecin compounds. Camptothecin compounds are capable of inhibiting DNA topoisomerase I. Camptothecin compounds include camptothecin, derivatives of camptothecin and analogs of camptothecin. Camptothecin compounds are known in the art and include, for example, camptothecin, topotecan (available as HYCAMTIN® from SmithKline Beecham Pharmaceuticals), CPT-11 (also called irinotecan), 9-aminocamptothecin, and the like. Other camptothecin compounds (or other compounds that can inhibit DNA topoisomerase I) that become approved by the FDA or foreign counterparts thereof are also preferred for use in the methods and compositions of the present invention. Other camptothecin compounds that can be used in the present invention include those described in, for example, J. Med. Chem., 29:2358-2363 (1986); J. Med. Chem., 23:554 (1980); J. Med. Chem., 30:1774 (1987); European Patent Application Nos. 0 418 099, 0 088 642, and 0 074 770; and U.S. Pat. Nos. 5,633,016, 5,004,758, 4,604,463, 4,473,692, 4,545,880, 4,513,138, 4,399,276, 6,121,451, 6,121,278, 6,121,277, 6,121,275, 6,121,263, 6,107,486, 6,100,273, 6,096,336, 6,093,721, 6,063,801, 6,046,209, 6,040,313, 6,034,243, 6,028,078, 5,998,426, 5,990,120, 5,985,888, 5,981,542, 5,972,955, 5,968,943, 5,958,937, 5,955,467, 5,948,797, 5,935,967, 5,932,709, 5,932,588, 5,922,877, 5,916,897, 5,916,896, 5,910,491, 5,900,419, 5,892,043, 5,889,017, 5,880,133, 5,859,023, 5,859,022, 5,856,333, 5,843,954, 5,840,899, 5,837,673, 5,834,012, 5,807,874, 5,801,167, 5,786,344, 5,773,522, 5,767,142, 5,744,605, 5,734,056, 5,731,316, 5,726,181, 5,677,286, 5,674,874, 5,674,873, 5,670,500, 5,633,177, 5,652,244, 5,646,159, 5,633,260, 5,614,628, 5,604,233, 5,602,141, 5,597,829, 5,559,235, 5,552,154, 5,541,327, 5,525,731, 5,496,952, 5,475,108, 5,468,859, 5,468,754, 5,459,269, 5,447,936, 5,446,047, 5,401,747, 5,391,745, 5,364,858, 5,340,817, 5,244,903, 5,227,380, 5,200,524, 5,191,082, 5,180,722, 5,162,532, 5,122,606, 5,122,526, 5,106,742, 5,061,800, 5,053,512, 5,049,668, 5,004,758, 4,981,968, 4,943,579, 4,939,255, 4,914,205, 4,894,456, RE 32,518, U.S. Pat. Nos. 4,604,463, 4,513,138, 4,473,692, 4,399,282, 4,399,276, and 4,031,098, the disclosures of which are incorporated by reference herein in their entirety.

The immunoconjugates and chemotherapeutic agents of the present invention can be administered in vitro, in vivo and/or ex vivo to treat patients and/or to modulate the growth of selected cell populations including, for example, cancer of the lung, breast, colon, prostate, kidney, pancreas, brain, bones, ovary, testes, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like. Preferably, the immunoconjugates and chemotherapeutic agents of the invention are administered in vitro, in vivo and/or ex vivo to treat cancer in a patient and/or to modulate the growth of cancer cells, including, for example, cancer of the lung, breast, colon, prostate, kidney, pancreas, brain, bones, ovary, testes, and lymphatic organs; more preferably lung cancer or colon cancer. In a most preferred embodiment, the lung cancer is small cell lung cancer (SCLC).

"Modulating the growth of selected cell populations" includes inhibiting the proliferation of selected cell populations (e.g., SCLC cells, NCI N417 cells, SW-2 cells, NCI-H441 cells, HT-29 cells, and the like) from dividing to produce more cells; reducing the rate of increase in cell division as compared, for example, to untreated cells; killing selected cell populations; and/or preventing selected cell populations (such as cancer cells) from metastasizing. The growth of selected cell populations can be modulated in vitro, in vivo or ex vivo.

In the methods of the present invention, the immunoconjugates and chemotherapeutic agents can be administered in vitro, in vivo, or ex vivo separately or as components of the same composition. The immunoconjugates and chemotherapeutic agents can be used with suitable pharmaceutically acceptable carriers, diluents, and/or excipients, which are well known, and can be determined by one of skill in the art as the clinical situation warrants. Examples of suitable carriers, diluents and/or excipients include: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The compounds and compositions described herein may be administered in appropriate form, preferably parenterally, more preferably intravenously. For parenteral administration, the compounds or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants. The compositions can also be in the form of sterile solid compositions which can be dissolved or dispersed in sterile water or any other injectable sterile medium.

The "therapeutically effective amount" of the chemotherapeutic agents and immunoconjugates described herein refers to the dosage regimen for inhibiting the proliferation of selected cell populations and/or treating a patient's disease, and is selected in accordance with a variety of factors, including the age, weight, sex, diet and medical condition of the patient, the severity of the disease, the route of administration, and pharmacological considerations, such as the activity, efficacy, pharmacokinetic and toxicology profiles of the particular compound used. The "therapeutically effective amount" can also be determined by reference to standard medical texts, such as the Physicians Desk Reference 1999 (53rd Ed.), the disclosure of which is incorporated by reference herein in its entirety. The patient is preferably an animal, more preferably a mammal, most preferably a human. The patient can be male or female, and can be an infant, child or adult.

Examples of suitable protocols of immunoconjugate administration are as follows. Immunoconjugates can be given daily for about 5 days either as an i.v. bolus each day for about 5 days, or as a continuous infusion for about 5 days. Alternatively, they can be administered once a week for six weeks or longer. As another alternative, they can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period. Dosages will be about 10 μg to about 1000 mg/kg per person, i.v. (range of about 100 ng to about 10 mg/kg). About one to about four weeks after treatment, the patient can receive a second course of treatment. Specific clinical protocols with regard to route of administration, excipients, diluents, dosages, and times can be determined by the skilled artisan as the clinical situation warrants.

The present invention also provides pharmaceutical kits comprising one or more containers filled with one or more of the ingredients of the pharmaceutical compounds and/or compositions of the present invention, including, one or more immunoconjugates and one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

EXAMPLES

The following examples are for purposes of illustration only, and are not intended to limit the scope of the invention or claims.

Example 1

The maytansinoid DM1 was conjugated to the humanized monoclonal antibody N901.

Ansamitocin P-3, provided by Takeda (Osaka, Japan) was converted to the disulfide-containing maytansinoid DM1, as described herein and in U.S. Pat. No. 5,208,020, the disclosure of which is incorporated by reference herein in its entirety.

Ansamitocin P-3

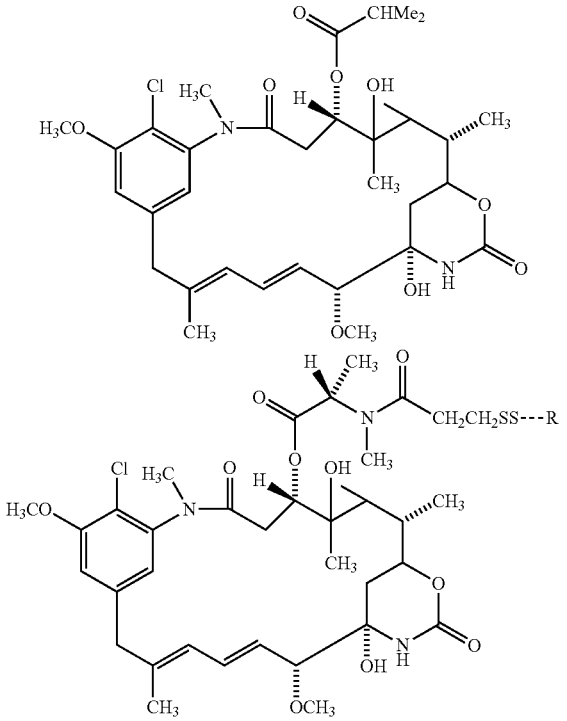

Humanized N901 is an antibody that binds to the CD56 antigen expressed on all human small cell lung cancer (SCLC) tissues, neuroblastomas and carcinoid tumors (Doria et al, Cancer 62:1839-1845 (1988); Kibbelaar et al, Eur. J. Cancer, 27:431-435 (1991);Rygaard et al, Br. J. Cancer, 65:573-577 (1992)).

Humanized N901 was modified with N-succinimidyl-4-[2-pyridyldithio]-pentanoate (SPP) to introduce dithiopyridyl groups. Alternatively, N-succinimidyl-3-[2-pyridyldithio]-propanoate (SPDP) can be used. The antibody (8 mg/mL) in 50 mM potassium phosphate buffer, pH 6.5, containing NaCl (50 mM) and EDTA (2 mM) was treated with SPP (5.6 molar equivalents in ethanol). The final ethanol concentration was 5% (v/v). After 90 minutes at ambient temperature, the reaction mixture was gel filtered through a Sephadex G25 column equilibrated in the above buffer. Antibody-containing fractions were pooled and the degree of modification was determined by treating a sample with dithiothreitol and measuring the change in absorbance at 343 nm (release of 2-mercaptopyridine with $\epsilon_{343\ nm}$=8, 080 $M^{-1}$). Recovery of the antibody was typically 90%, with 4.8 pyridyldithio groups linked per antibody molecule.

The modified antibody was diluted with 50 mM potassium phosphate buffer, 6.5, containing NaCl (50 mM) and EDTA (2 mM) to a final concentration of 2.5 mg/mL. DM1 (1.7 eq.) in dimethylacetamide (DMA, 3% v/v in final reaction mixture) was then added to the modified antibody solution. The reaction proceeded at ambient temperature under argon for 20 hours.

The reaction mixture was then loaded on to a Sephacryl S300 gel filtration column equilibrated with phosphate-buffered saline (PBS, pH 6.5). The major peak comprised monomeric hu901-DM1. The number of DM1 drug molecules linked per antibody molecule was determined by measuring the absorbance at 252 nm and 280 nm and found to be 3.9 DM1 molecules per antibody molecule.

Example 2

In this experiment, a low, non-curative dose of huN901-DM1 was used with an optimal does of paclitaxel (Sigma Chemical Co., St. Louis, Mo.). SCID mice (7 animals per group) were inoculated subcutaneously with NCI N417 cells ($8\times10^6$ cells/animal). After the tumors were well-established (average tumor size was approximately 100 $mm^3$), one group of animals was treated with huN901-DM1 at a DM1 dose of 75 μg/kg/d×5, administered i.v. everyday. A second group of animals was treated with paclitaxel at a dose of 10 mg/kg/d×5, administered by i.p. everyday. A third group of animals was treated with huN901-DM1 and paclitaxel using the same dose and schedule used for the individual agents. A fourth, control group of animals was left untreated. Tumor size was measured as described by Liu et al, Proc. Natl. Acad. Sci., 93:8618-8623 (1996). Animals were also monitored for weight loss as an indicator of signs of toxicity.

Figure 5:
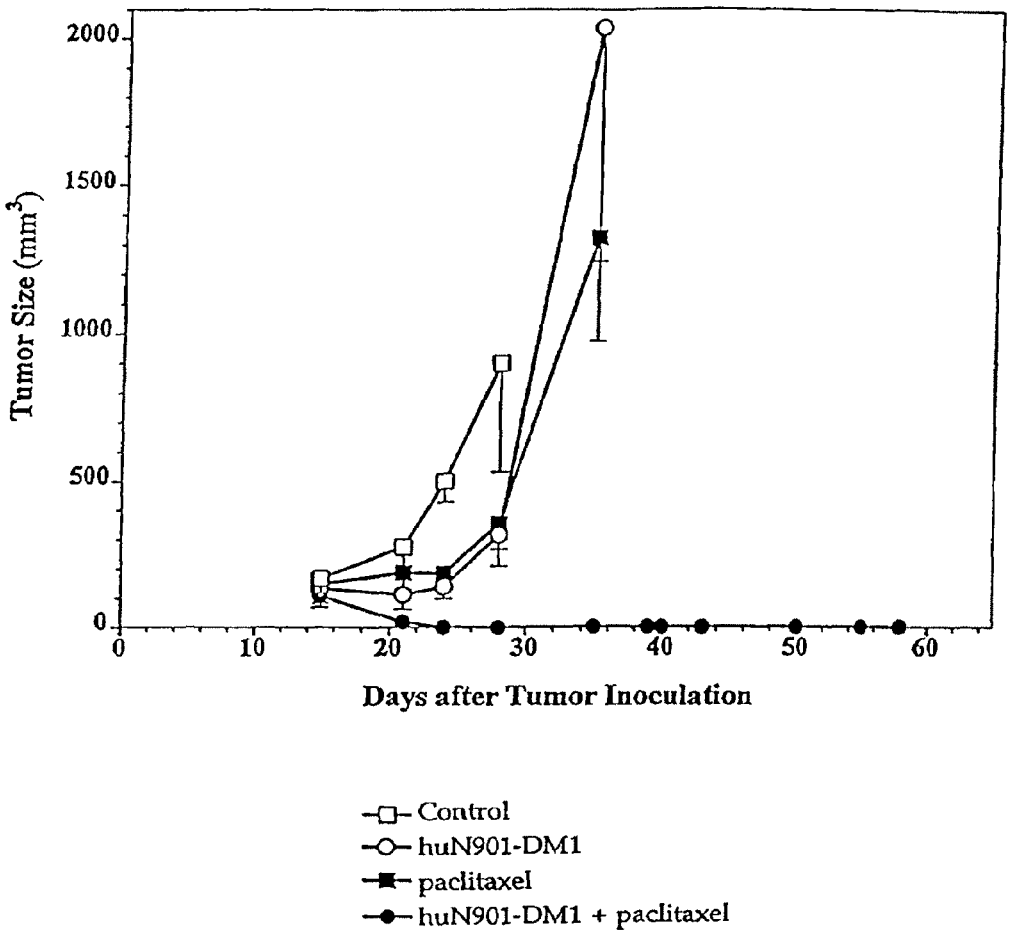
FIG. 5 is a graph comparing the anti-tumor activity of (i) a control, (ii) huN901-DM1, (iii) paclitaxel, and (iv) the combination of huN901-DM1 and paclitaxel, against small cell lung cancer xenografts in SCID mice.

The results of the experiment are shown in FIG. 5. In the control group of animals, the tumors grew rapidly to a size of about 900 $mm^3$ by Day 28 post-tumor inoculation. In animals treated with either huN901-DM1 or paclitaxel, there was a modest anti-tumor effect with a tumor growth delay of 4 days in each case. In the animals treated with huN901-DM1 and paclitaxel, the tumors disappeared with complete regression lasting 58 days. Importantly, there was no evidence of toxicity in the animals. These data demonstrate that treatment with huN901-DM1 and paclitaxel has an unexpectedly superior (e.g., synergistic) anti-tumor effect.

Example 3

In this experiment, a low, non-curative dose of huN901-DM1 was used with an optimal dose of cisplatin (Sigma Chemical Co., St. Louis, Mo.) and etoposide (Sigma Chemical Co., St. Louis, Mo.). SCID mice (7 animals per group) were inoculated subcutaneously with NCI N417 cells ($8\times10^6$ cells/animal). After the tumors were well-established (average tumor size was approximately 100 $mm^3$), one group of animals was treated with huN901-DM1 at a DM1 dose of 75 μg/kg/d×5, administered i.v. everyday. A second group of animals was treated with cisplatin (at a dose of 2 mg/kg/d×3, administered by i.v. ever other day) and etoposide (at a dose of 8 mg/kg/d×3, administered every other day). A third group of animals was treated with huN901-DM1, cisplatin and etoposide using the same dose and schedule used for a the individual agents. A fourth, control group of animals was left untreated. Tumor size was measured as described by Liu et al, Proc. Natl. Acad. Sci., 93:8618-8623 (1996). Animals were also monitored for weight loss as an indicator of signs of toxicity.

Figure 6:
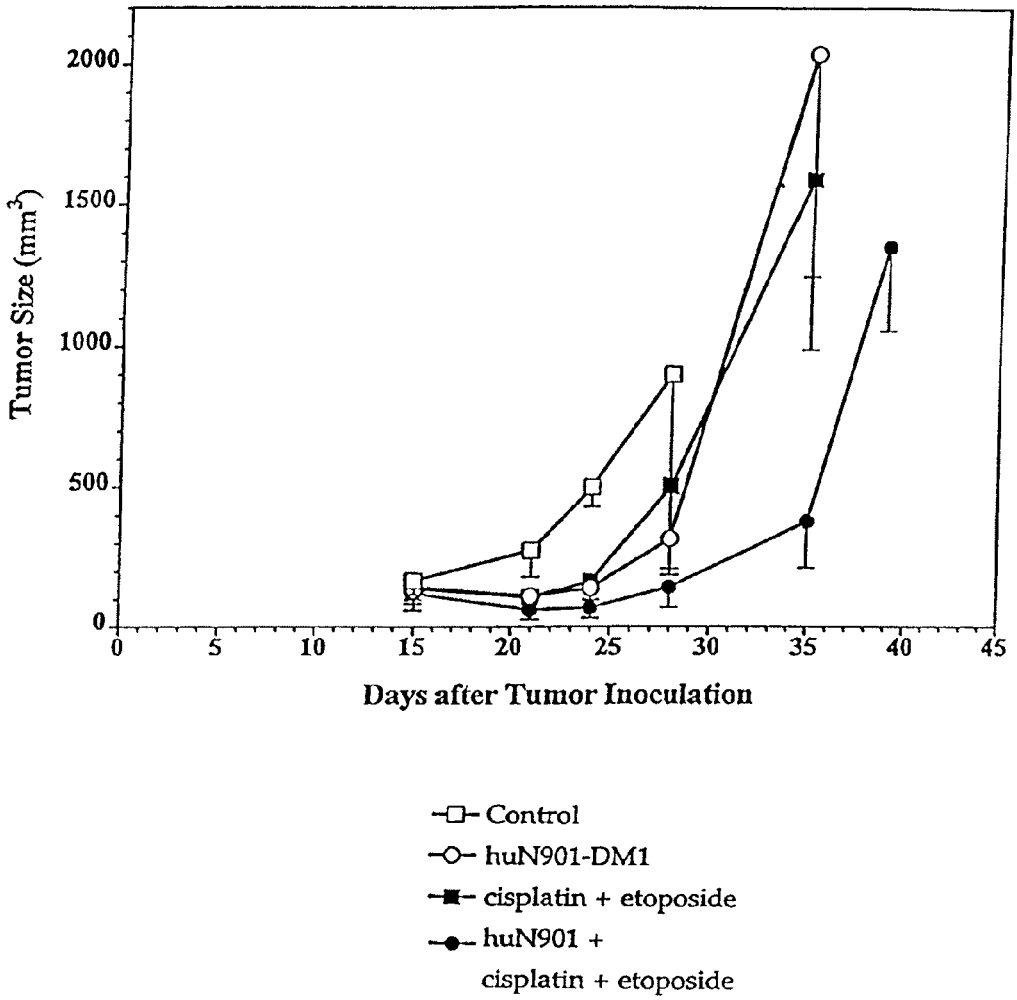
FIG. 6 is a graph comparing the anti-tumor activity of (i) a control, (ii) huN901-DM1, (iii) the combination of cisplatin and etoposide, and (iv) the combination of huN901-DM1, cisplatin and etoposide, against small cell lung cancer xenografts in SCID mice.

The results of the experiment are shown in FIG. 6. In the control group of animals, the tumors grew rapidly to a size of about 900 $mm^3$ by Day 28 post-tumor inoculation. In animals treated with either huN901-DM1 or cisplatin and etoposide, there was a modest anti-tumor effect with a tumor growth delay of 4 days in each case. In the animals treated with huN901-DM1, cisplatin and etoposide, there was a tumor growth delay of 12 days, which is 50% longer than what one would expect for an additive anti-tumor effect of the individual compounds. Importantly, there was no evidence of toxicity in the animals. These data demonstrate that treatment with huN901-DM1, cisplatin, and etoposide has an unexpectedly superior (e.g., synergistic) anti-tumor effect.

Example 4

The anti-tumor effect of a combination of a low dose of huN901-DM1 and docetaxel (available as TAXOTERE® from Aventis) was evaluated in an established subcutaneous xenograft model of small cell lung cancer. SCID mice (24 animals) were inoculated with human small cell lung cancer SW-2 cells ($8\times10^6$ cells/animal) injected subcutaneously into the right flank of the mice. When the tumors reached about 100 $mm^3$ in size (10 days after tumor cell inoculation), the mice were randomly divided into four groups (6 animals per group). The first group of mice was treated with docetaxel (5 mg/kg×5, q2d) administered i.v. A second group of animals was treated with huN901-DM1 (DM1 dose of 75 μg/kg×5, qd) administered i.v. The third group of mice received a combination of docetaxel and huN901-DM1, using the same doses and schedules as in groups 1 and 2. A control group of animals received phosphate-buffered saline (PBS) using the same schedule as the animals in group 2. Tumor growth was monitored by measuring tumor size twice per week. Tumor size was calculated with the formula: length×width×height×½.

Figure 7:
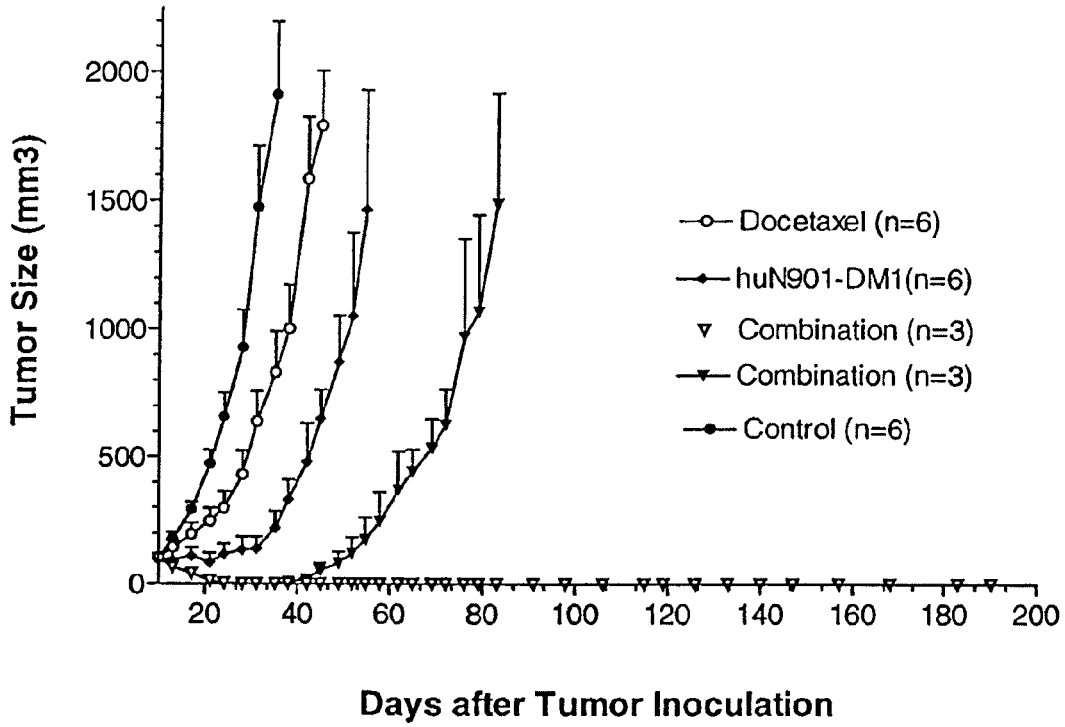
FIG. 7 is a graph comparing the anti-tumor activity of (i) a control, (ii) huN901-DM1, (iii) docetaxel, and (iv) the combination of huN901-DM1 and docetaxel, against small cell lung cancer xenografts in SCID mice.

The change in tumor size is shown in FIG. 7. In the control group of animals, tumors grew rapidly to about 1000 $mm^3$ in 26 days. Treatment with docetaxel alone, or a low dose of huN901-DM1 alone, resulted in tumor growth delays of 8 days and 20 days, respectively. In contrast, treatment with the combination of docetaxel and huN901-DM1 showed a remarkable anti-tumor effect resulting in complete tumor regression in all the treated animals. In 3 out of 6 animals in this treatment group, the tumor was eradicated—resulting in cures lasting greater than 200 days. In the remaining 3 animals in this group, there was a tumor growth delay of 52 days, which is 24 days longer than the calculated additive effect. Thus, the combination of docetaxel and huN901-DM1 shows an unexpectedly superior (e.g., synergistic) anti-tumor effect in this human SCLC xenograft model.

Example 5

The anti-tumor effect of a combination of a low dose of huN901-DM1 and topotecan (available as HYCAMTIN® from SmithKline Beecham Pharmaceuticals), one of the approved drugs for the treatment of small cell lung cancer (SCLC) in humans, was evaluated in an established subcutaneous xenograft model of SCLC. SCID mice (24 animals) were inoculated with human small cell lung cancer SW-2 cells ($8\times10^6$ cells/animal) injected subcutaneously into the right flank of the mice. When the tumors reached about 80 $mm^3$ in size, the mice were randomly divided into four groups (6 animals per group). The first group of mice was treated with topotecan (1.4 mg/kg×5, qd) administered i.v. A second group of animals was treated with huN901-DM1 (DM1 dose of 100 μg/kg×5, qd) administered i.v. The third group of mice received a combination of topotecan and huN901-DM1, using the same doses and schedules as in groups 1 and 2. A control group of animals received phosphate-buffered saline (PBS) using the same schedule as the animals in group 2. Tumor growth was monitored by measuring tumor size twice per week. Tumor size was calculated using the formula: length×width×height×½.

Figure 8:
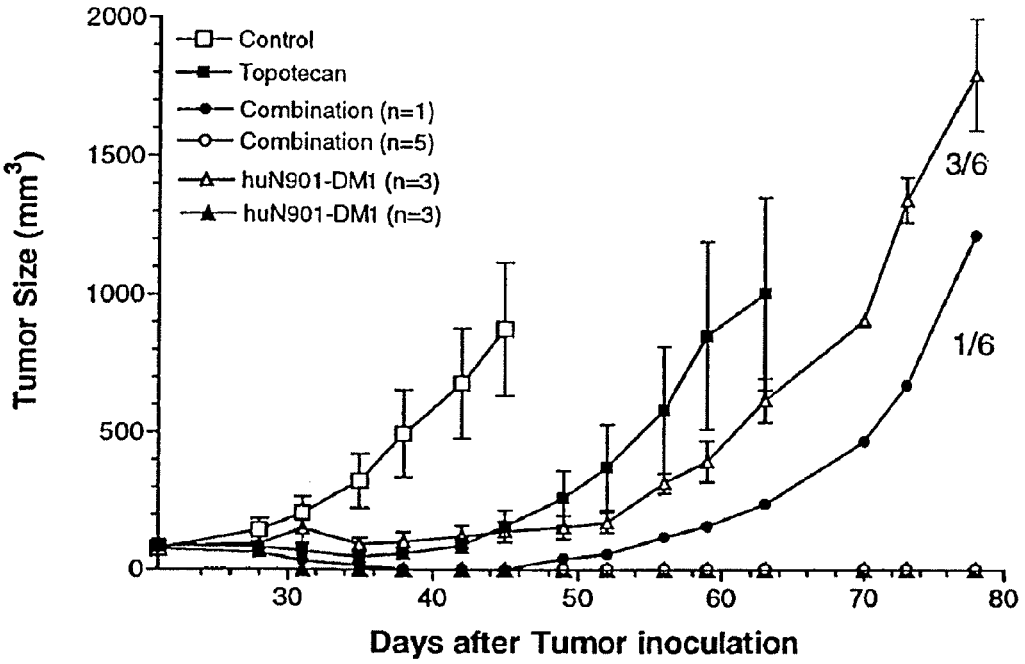
FIG. 8 is a graph comparing the anti-tumor activity of (i) a control, (ii) huN901-DM1, (iii) topotecan, and (iv) the combination of huN901-DM1 and topotecan, against small cell lung cancer xenografts in SCID mice.

The change in tumor size is shown in FIG. 8. In the control group of animals, tumors grew to about 800 $mm^3$ in 44 days. Treatment with topotecan alone resulted in tumor growth delays of 12 days. Treatment with a low dose of huN901-DM1 alone resulted in a tumor-growth delay of 34 days in 3 out of 6 animals. The remaining 3 animals in this group had complete tumor regressions. Treatment with the combination of topotecan and huN901-DM1 showed a remarkable anti-tumor effect resulting in complete tumor regression in 5 out of the 6 treated animals. These animals were tumor-free on day 78, the last measurement point. Thus, the combination of topotecan and huN901-DM1 is unexpectedly superior (e.g., synergistic) when compared to the single agents in this human SCLC xenograft model.

Example 6

The anti-tumor effect of a combination of a low dose of huC242-DM1 (manufactured by ImmunoGen, Inc. following the procedures described in U.S. Pat. No. 5,208,020, the disclosure of which is incorporated by reference herein in its entirety, and also described in Example 1) and paclitaxel (Sigma Chemical Co., St. Louis, Mo.) was evaluated in an established subcutaneous xenograft model of non-small cell lung cancer. SCID mice (24 animals) were inoculated with human lung adenocarcinoma NCI-H441 cells ($8\times10^6$ cells/animal), injected subcutaneously into the right flank of the mice. When the tumors reached about 125 $mm^3$ in size (4 days after tumor cell inoculation), the mice were randomly divided into four groups (6 animals per group). The first group of mice was treated with paclitaxel (15 mg/kg×5, q2d) administered i.p. A second group of animals was treated with huC242-DM1 (DM1 dose of 75μg/kg×5, qd) administered i.v. The third group of mice received a combination of paclitaxel and huC242-DM1, using the same doses and schedules as in groups 1 and 2. In the combination group, the huC242-DM1 conjugate was administered 2 hours after the paclitaxel. A control group of animals received phosphate-buffered saline (PBS) using the same schedule as the animals in group 2. Tumor growth was monitored by measuring tumor size twice per week. Tumor size was calculated using the formula: length×width×height×½.

Figure 9:
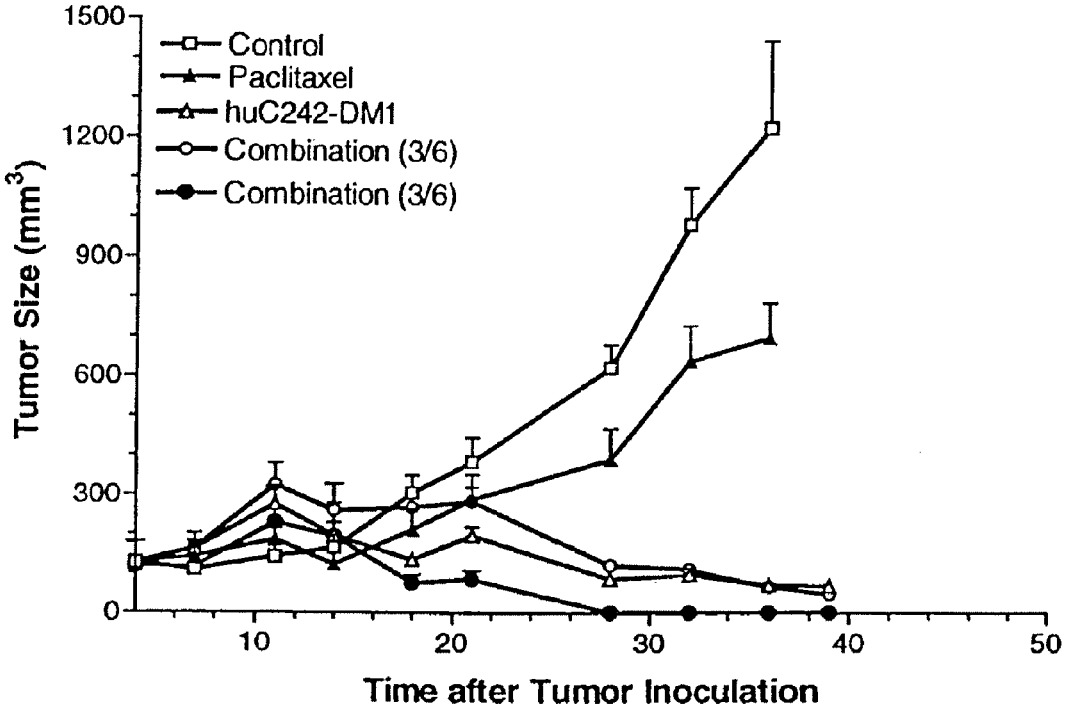
FIG. 9 is a graph comparing the anti-tumor activity of (i) a control, (ii) huC242-DM1, (iii) paclitaxel, and (iv) the combination of huC242-DM1 and paclitaxel, against human lung adenocarcinoma xenografts in SCID mice.

The change in tumor size is shown in FIG. 9. In the control group of animals, tumors grew rapidly to about 1000 $mm^3$ in 32 days. Treatment with paclitaxel alone, resulted in a small tumor growth delay of 4 days. Treatment with huC242-DM1 resulted in shrinkage of the tumor, but none of the 6 treated animals showed complete tumor regression. Treatment with a combination of paclitaxel and huC242-DM1 showed a greater anti-tumor effect resulting in complete tumor regression, with 3 out of the 6 animals showing no evidence of tumor. The remaining 3 animals in this group showed a significant shrinkage in the tumor. Thus, the combination of paclitaxel and huC242-DM1 is unexpectedly superior (e.g., synergistic) in this human SCLC lung adenocarcinoma xenograft model.

Example 7

The anti-tumor effect of a combination of a low dose of huC242-DM1 (manufactured by ImmunoGen, Inc. following the methods described in U.S. Pat. No. 5,208,020, the disclosure of which is incorporated by reference herein in its entirety, and also described in Example 1) and paclitaxel (Sigma Chemical Co., St. Louis, Mo.) was evaluated in an established subcutaneous xenograft model of non-small cell lung cancer. SCID mice (32 animals) were inoculated with human colon cancer HT-29 cells ($8\times10^6$ cells/animal), injected subcutaneously into the right flank of the mice. When the tumors reached about 80 $mm^3$ in size, the mice were randomly divided into four groups (8 animals per group). The first group of mice was treated with CPT-11 (50 mg/kg×2, q3d) administered i.v. The second group of animals was treated with murine C242-DM1 (DM1 dose of 75 μg/kg×5, qd) administered i.v. The third group of mice received a combination of CPT-11 and C242-DM1, using the same doses and schedules as in groups 1 and 2. A control group of animals received phosphate-buffered saline (PBS) using the same schedule as the animals in group 2. Tumor growth was monitored by measuring tumor size twice per week. Tumor size was calculated using the formula: length×width×height×½.

Figure 10:
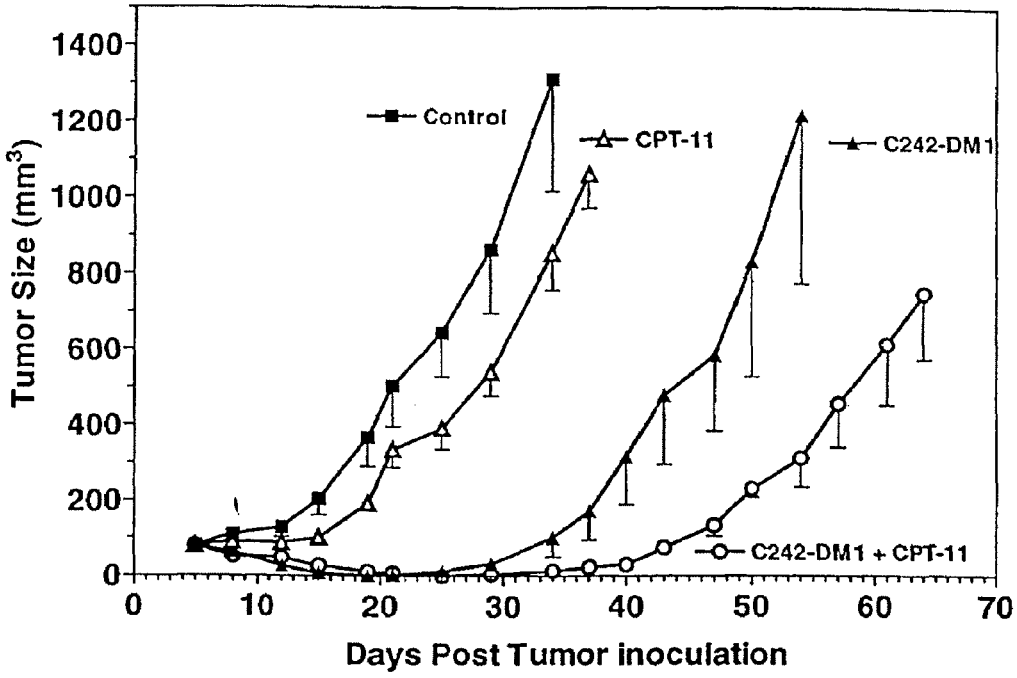
FIG. 10 is a graph comparing the anti-tumor activity of (i) a control, (ii) huC242-DM1, (iii) CPT-11 (also called irinotecan), and (iv) the combination of huC242-DM1 and CPT-11, against human colon cancer xenografts in SCID mice.

The change in tumor size is shown in FIG. 10. In the control group of animals, tumors grew rapidly to about 1000 $mm^3$ in 31 days. Treatment with CPT-11 alone resulted in a small tumor growth delay of 6 days. Treatment with C242-DM1 resulted in a delay in tumor growth of 22 days. Treatment with a combination of CPT-11 and C242-DM1 showed an unexpectedly superior anti-tumor effect resulting in a tumor growth delay of 38 days, which is 10 days longer than the calculated additive effect. Thus, the combination of CPT-11 and C242-DM1 is unexpectedly superior (e.g., synergistic) in this human colon cancer xenograft model.

Each of the patents and publications cited in the specification is incorporated by reference herein in its entirety.

Various modifications of the invention, in addition to those described herein, will be apparent to one skilled in the art from the foregoing description. Such modifications are intended to fall within the scope of the appended claims.

What is claimed is:

1. A pharmaceutical composition comprising a synergistic combination of at least one chemotherapeutic agent and at least one immunoconjugate; wherein the immunoconjugate comprises at least one maytansinoid compound linked to a monoclonal antibody or fragment thereof; wherein the monoclonal antibody or fragment thereof binds to an antigen expressed by a cancer cell, and wherein the chemotherapeutic agent is a taxane compound, an epothilone compound, a platinum compound, an epipodophyllotoxin compound, a camptothecin compound, or a mixture of two or more thereof, *and wherein the monoclonal antibody or fragment thereof binds to a CD56 antigen*.

[2. The pharmaceutical composition of claim 1, wherein the chemotherapeutic agent is a taxane compound, a platinum compound, an epipodophyllotoxin compound, a camptothecin compound, or a mixture of two or more thereof.]

[3. The pharmaceutical composition of claim 1, wherein the chemotherapeutic agent is paclitaxel, docetaxel, epothilone A, epothilone B, epothilone C, epothilone D, epothilone E, epothilone F, cisplatin, carboplatin, oxaliplatin, iproplatin, ormaplatin, tetraplatin, etoposide, teniposide, camptothecin, topotecan, irinotecan, 9-aminocamptothecin, or a mixture of two or more thereof.]

[4. The pharmaceutical composition of claim 1, wherein the chemotherapeutic agent is paclitaxel, cisplatin, etoposide, docetaxel, topotecan, or a mixture of two or more thereof.]

[5. The pharmaceutical composition of claim 1, wherein the monoclonal antibody or fragment thereof binds to a CD56 antigen.]

[6. The pharmaceutical composition of claim 1, wherein the monoclonal antibody or fragment thereof is at least one of Fv, Fab, Fab' or $F(ab')_2$.]

7. [The pharmaceutical composition of claim 1,] *A pharmaceutical composition comprising a synergistic combination of at least one chemotherapeutic agent and at least one immunoconjugate; wherein the immunoconjugate comprises at least one maytansinoid compound linked to a monoclonal antibody or fragment thereof, wherein the monoclonal antibody or fragment thereof binds to an antigen expressed by a cancer cell, wherein the chemotherapeutic agent is a taxane compound, an epothilone compound, a platinum compound, an epipodophyllotoxin compound, a camptothecin compound, or a mixture of two or more thereof, and* wherein the monoclonal antibody or fragment thereof is humanized N901.

8. [The pharmaceutical composition of claim 1,] *A pharmaceutical composition comprising a synergistic combination of at least one chemotherapeutic agent and at least one immunoconjugate; wherein the immunoconjugate comprises at least one maytansinoid compound linked to a monoclonal antibody or fragment thereof, wherein the monoclonal antibody or fragment thereof binds to an antigen expressed by a cancer cell, wherein the chemotherapeutic agent is a taxane compound, an epothilone compound, a platinum compound, an epipodophyllotoxin compound, a camptothecin compound, or a mixture of two or more thereof, and* wherein the monoclonal antibody or fragment thereof is humanized C242.

[9. The pharmaceutical composition of claim 1, wherein the immunoconjugate comprises at least one maytansinoid compound of formula (IV):

(IV)

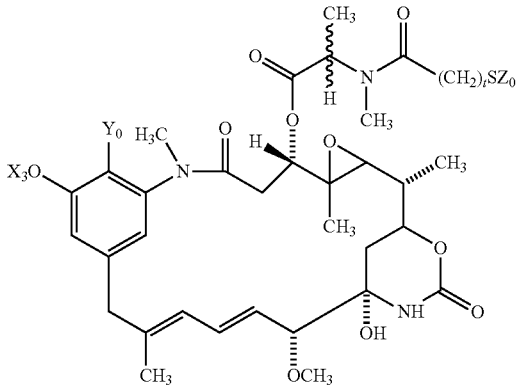

wherein is $Z_0$ is H or SR; R is methyl, linear alkyl, branched alkyl, cyclic alkyl, simple or substituted aryl or heterocyclic; t is 1, 2 or 3; $Y_0$ is chlorine or hydrogen; and $X_3$ is hydrogen or methyl.]

[10. The pharmaceutical composition of claim 9, wherein $Z_0$ is H; t is 2; $Y_0$ is chlorine; and $X_3$ is methyl.]

[11. The pharmaceutical composition of claim 1, wherein the immunoconjugate is of the formula:

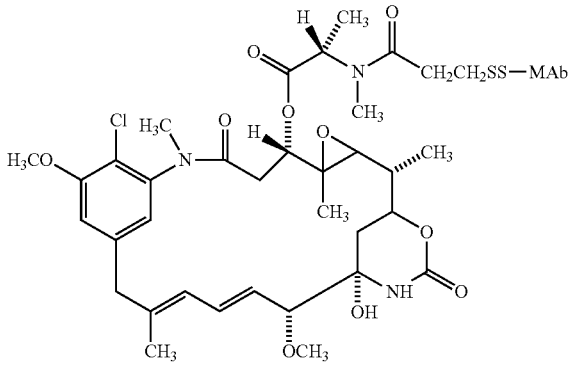

wherein MAb is a monoclonal antibody or fragment thereof that binds to an antigen expressed by the cancer cell.]

[12. A pharmaceutical composition comprising a synergistic combination of at least one chemotherapeutic agent and at least one immunoconjugate; wherein the chemotherapeutic agent is a taxane compound, an epothilone compound, a platinum compound, an epipodophyllotoxin compound, a camptothecin compound, or a mixture of two or more thereof; and wherein the immunoconjugate is:

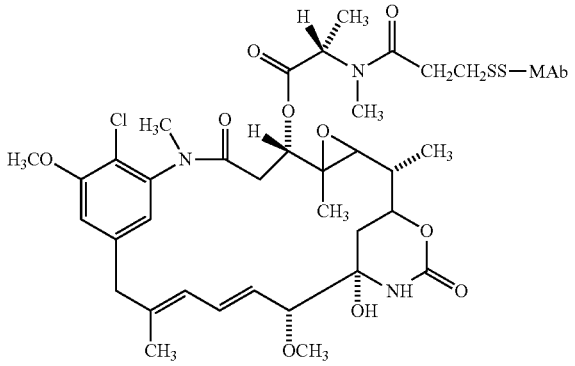

wherein MAb is a monoclonal antibody or fragment thereof that binds to an antigen expressed by a cancer cell.]

13. A pharmaceutical composition comprising a synergistic combination of (i) at least one chemotherapeutic agent selected from the group consisting of paclitaxel, docetaxel, cisplatin, etoposide, topotecan and irinotecan and (ii) an immunoconjugate comprising a maytansinoid and a humanized monoclonal antibody selected from the group consisting of N901 and C242.

14. The pharmaceutical composition of claim 13, wherein the maytansinoid is a compound of formula (IV):

[

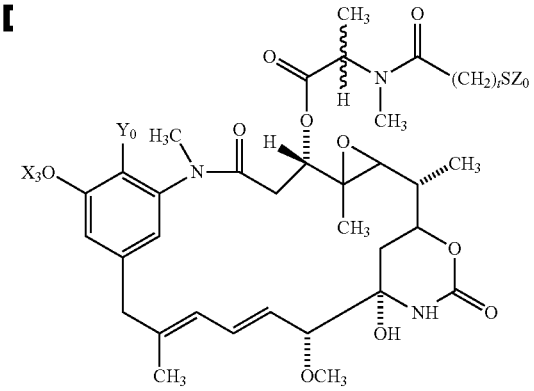

]

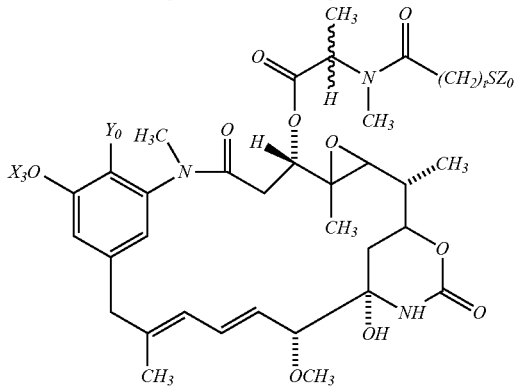

wherein $Z_0$ is H or SR; wherein R is methyl, linear alkyl, branched alkyl, cyclic alkyl, simple or substituted aryl or heterocyclic; t is 1, 2 or 3; $Y_0$ is chlorine or hydrogen; and $X_3$ is hydrogen or methyl.

[15. A pharmaceutical composition comprising a synergistic combination of (i) at least one chemotherapeutic agent selected from the group consisting of paclitaxel, docetaxel, cisplatin, etoposide, topotecan and irinotecan and (ii) an immunoconjugate comprising a maytansinoid and a humanized monoclonal antibody or fragment thereof that binds to an antigen expressed by a small cell lung cancer cell, a non small cell lung cancer cell or a colorectal cancer cell.]

[16. The pharmaceutical composition of claim 15, wherein the maytansinoid is a compound of formula (IV):

(IV)

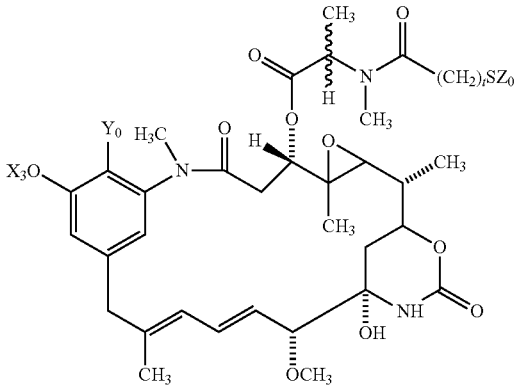

wherein $Z_0$ is H or SR; wherein R is methyl, linear alkyl, branched alkyl, cyclic alkyl, simple or substituted aryl or heterocyclic; t is 1, 2 or 3; $Y_0$ is chlorine or hydrogen; and $X_3$ is hydrogen or methyl.]

* * * * *

UNITED STATES PATENT AND TRADEMARK OFFICE

CERTIFICATE OF CORRECTION

PATENT NO. : RE44,704 E
APPLICATION NO. : 13/613743
DATED : January 14, 2014
INVENTOR(S) : Ravi V. J. Chari et al.

It is certified that error appears in the above-identified patent and that said Letters Patent is hereby corrected as shown below:

In the Claims

In Column 24, Claim 1, line 60,

"expressed by a cancer cell, and wherein the chemotherapeutic", should be

-- expressed by a cancer cell, wherein the chemotherapeutic --.

Signed and Sealed this
Thirteenth Day of May, 2014

Michelle K. Lee

Michelle K. Lee
*Deputy Director of the United States Patent and Trademark Office*

UNITED STATES PATENT AND TRADEMARK OFFICE

CERTIFICATE OF CORRECTION

PATENT NO. : RE44,704 E
APPLICATION NO. : 13/613743
DATED : January 14, 2014
INVENTOR(S) : Ravi V. J. Chari et al.

It is certified that error appears in the above-identified patent and that said Letters Patent is hereby corrected as shown below:

On the Title Page, Item [73],

"(73) Assignee: Immunogen, Inc., Waltham, MA (US)", should be -- (73) Assignee: ImmunoGen, Inc., Waltham, MA (US) --.

Signed and Sealed this
Twenty-third Day of September, 2014

Michelle K. Lee

Michelle K. Lee
*Deputy Director of the United States Patent and Trademark Office*